United States Patent [19]

Branca et al.

[11] Patent Number: 5,278,148

[45] Date of Patent: Jan. 11, 1994

[54] AMINO ACID DERIVATIVES USEFUL FOR TREATING HIGH BLOOD PRESSURE

[75] Inventors: Quirico Branca; Hans P. Märki, both of Basel, Switzerland; Werner Neidhart, Freiburt im Breisgau, Fed. Rep. of Germany; Henri Ramuz, Birsfelden, Switzerland; Wolfgang Wostl, Grenzach-Wyhlen, Fed. Rep. of Germany

[73] Assignee: Hoffmann-La Roche Inc., Nutley, N.J.

[21] Appl. No.: 499,852

[22] Filed: Mar. 27, 1990

[30] Foreign Application Priority Data

Mar. 28, 1989 [CH] Switzerland ............ 1118/89

[51] Int. Cl.$^5$ ............ A61K 37/02; A61K 37/43; C07K 5/06; C07K 5/08; C07C 233/08; C07C 235/02; C07C 237/02

[52] U.S. Cl. ............ 514/19; 514/365; 514/400; 514/407; 514/438; 514/530; 514/540; 514/548; 514/551; 514/616; 514/620; 514/626; 548/214; 548/335.5; 548/338.1; 548/373.1; 548/375.1; 548/336.5; 549/75; 549/76; 549/77; 560/19; 560/37; 560/38; 560/155; 560/157; 560/159; 560/169; 564/164; 564/192; 564/193; 564/194; 564/196; 564/197

[58] Field of Search ............ 548/336, 335.5, 338.1, 548/373.1, 373.5, 336.5, 214; 514/397, 365, 399, 400, 407, 438, 530, 540, 548, 551, 19, 620, 616, 626; 549/75, 76, 77; 560/19, 37, 38, 155, 157, 169; 564/164, 192, 193, 194, 196, 197

[56] References Cited

U.S. PATENT DOCUMENTS

| | | | |
|---|---|---|---|
| 4,613,676 | 9/1986 | Fuhrer et al. ............ | 560/39 |
| 4,713,445 | 12/1987 | Szelke et al. ............ | 530/330 |
| 4,725,583 | 2/1988 | Luly et al. ............ | 514/18 |
| 4,727,060 | 2/1988 | Buhlmayer et al. ............ | 514/18 |
| 4,749,781 | 6/1988 | Gordon ............ | 530/323 |
| 4,826,815 | 5/1989 | Luly et al. ............ | 514/19 |
| 4,826,958 | 5/1989 | Sham ............ | 530/331 |
| 4,837,204 | 6/1989 | Rosenberg ............ | 514/18 |
| 4,845,079 | 7/1989 | Luly et al. ............ | 514/18 |
| 4,857,507 | 8/1989 | Rosenberg et al. ............ | 514/18 |
| 4,857,650 | 8/1989 | Iizuka et al. ............ | 548/336 |
| 4,885,292 | 12/1989 | Ryono et al. ............ | 514/397 |
| 4,931,591 | 6/1990 | Buhlmayer et al. ............ | 564/165 |

FOREIGN PATENT DOCUMENTS

12502/88 2/1988 Australia .

OTHER PUBLICATIONS

Burger, A. *Medicinal Chemistry*, Second Edition, New York (1960), pp. 565–571, 578–581, 600–601.
Plattner et al., *J. Med. Chem.*, (31) 1988, pp. 2277–2288.
Bolis et al., *J. Med. Chem.*, (30) 1987, pp. 1729–1737.
Denkewalter et al., *Progress in Drug Research*, vol. 10, 1966, pp. 510–512.

*Primary Examiner*—Floyd D. Higel
*Attorney, Agent, or Firm*—George M. Gould; George W. Johnston; John P. Parise

[57] ABSTRACT

Compounds of the formula

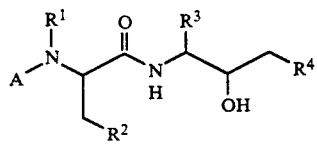

I wherein $R^1$ is hydrogen or methyl, $R^2$ is ethyl, propyl, isopropyl, imidazol-2-yl, imidazol-4-yl, pyrazol-3-yl, thiazol-4-yl, thien-2-yl, ethoxycarbonyl, t-butylcarbonylmethyl, benzyloxycarbonylmethyl or t-butoxy, $R^3$ is isobutyl, cyclohexylmethyl or benzyl, $R^4$ is nitro, amino or a group of the formula $-N(R^5)(R^6)$ and A is one of the groups

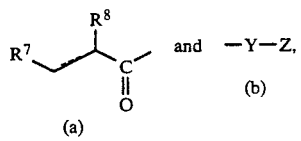

(a)     and   $-Y-Z$,
              (b)

wherein $R^5$ and $R^6$ is alkyl or alkoxyalkyl; or optionally substituted phenyl, phenylalkyl or phenylsulfonylalkyl (Abstract continued on next page.)

among others with the proviso that A is not group (b) when $R^6$ is alkanoyl, alkoxycarbonyl or arylalkoxycarbonyl, the dotted line can be an additional bond, $R^7$ is phenyl or substituted phenyl and $R^8$ is hydrogen or organocarbonylalkyl, with the proviso that $R^8$ is not alkoxycarbonylamino or arylalkoxycarbonylamino when $R^7$ is phenyl, benzyl or α-naphthyl, Y is a bivalent residue in the form of optically pure diastereomers, mixtures of diastereomers, diastereomeric racemates or mixtures of diastereomeric racemates as well as pharmaceutically usable salts thereof inhibit the activity of the natural enzyme renin and can accordingly be used in the control or prevention of high blood pressure and cardiac insufficiency.

16 Claims, No Drawings

AMINO ACID DERIVATIVES USEFUL FOR TREATING HIGH BLOOD PRESSURE

FIELD OF THE INVENTION

The present invention relates to amino acid derivatives which are useful for the treatment or control of high blood pressure and cardiac insufficiency.

SUMMARY OF THE INVENTION

An amino acid derivative of the formula

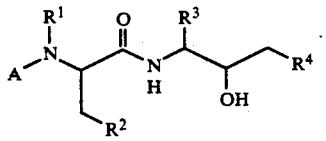

wherein $R^1$ is hydrogen or methyl, $R^2$ is ethyl, propyl, isopropyl, imidazol-2-yl, imidazol-4-yl, pyrazol-3-yl, thiazol-4-yl, thien-2-yl, ethoxycarbonyl, t-butylcarbonylmethyl, benzyloxycarbonylmethyl or t-butoxy, $R^3$ is isobutyl, cyclohexylmethyl or benzyl, $R^4$ is nitro, amino or a group of the formula $-N(R^5)(R^6)$ and A is one of the groups

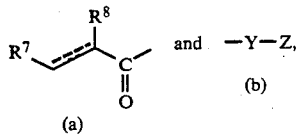

wherein $R^5$ is alkyl or alkoxyalkyl; or phenyl, phenylalkyl or phenylsulfonylalkyl, each of which may be mono- or multiply-substituted with alkyl, alkoxy, alkoxyalkoxy, alkanoyl, alkanoyloxy, hydroxy, halogen or trifluoromethyl; and $R^6$ is alkyl or alkoxyalkyl; or phenyl, phenylalkyl or phenylsulfonylalkyl, each of which may be mono- or multiply-substituted with alkyl, alkoxy, alkoxyalkoxy, alkanoyl, alkanoyloxy, hydroxy, halogen or trifluoromethyl; or alkanoyl, alkoxycarbonyl, arylalkoxycarbonyl, unsubstituted or substituted benzimidazolonyl or the residue of an amino acid, an acylated amino acid, a dipeptide or an acylated dipeptide, or $R^5$ and $R^6$ together with the nitrogen atom to which they are attached are a 5- or 6-membered heterocycle, a 5- or 6-membered lactam or a 5- or 6-membered imide, with the proviso that A is not group (b) when $R^6$ is alkanoyl, alkoxycarbonyl or arylalkoxycarbonyl, the dotted line can be an additional bond, $R^7$ is phenyl, phenyl which is mono- or multiply-substituted with alkyl, alkoxy, alkoxyalkoxy, alkanoyl, alkanoyloxy, hydroxy, halogen or trifluoromethyl, or benzyl or naphthyl and $R^8$ is hydrogen, alkoxycarbonylalkyl, alkylcarbonylalkyl, cycloalkylcarbonylalkyl, heterocycloalkylcarbonylalkyl, arylcarbonylalkyl, aminocarbonylalkyl, substituted aminocarbonylalkyl, aminoalkylcarbonylalkyl, substituted aminoalkylcarbonylalkyl, aminoalkylsulfonylalkyl, substituted aminoalkylsulfonylalkyl, alkoxycarbonylhydroxyalkyl, alkylcarbonylhydroxyalkyl, cycloalkylcarbonylhydroxyalkyl, heterocycloalkylcarbonylhydroxyalkyl, arylcarbonylhydroxyalkyl, aminocarbonylhydroxyalkyl, substituted aminocarbonylhydroxyalkyl, dialkoxyphosphoroxyalkyl, diphenyloxyphosphoroxyalkyl, arylalkyl, alkoxycarbonylamino, arylalkoxycarbonylamino, alkylthioalkyl, alkylsulfinylalkyl, alkylsulfonylalkyl, arylthioalkyl, arylsulfinylalkyl, arylsulfonylalkyl, arylalkylthioalkyl, arylalkylsulfinylalkyl or arylalkylsulfonylalkyl, with the proviso that $R^8$ is not alkoxycarbonylamino or arylalkoxycarbonylamino when $R^7$ is phenyl, benzyl or α-naphthyl, Y is the bivalent residue of phenylglycine, cyclohexylglycine, phenylalanine, cyclohexylalanine, 4-fluorophenylalanine, 4-chlorophenylalanine, tyrosine, O-methyltyrosine, α-naphthylalanine or homophenylalanine, each of which may be N- and/or α-methylated and is linked with Z at the N-terminal, and Z is hydrogen or acyl, in the form of optically pure diastereomers, mixtures of diastereomers, diastereomeric racemates or mixtures of diastereomeric racemates as well as a pharmaceutically usable salt of such a compound.

DETAILED DESCRIPTION OF THE INVENTION

The present invention relates to amino acid derivatives. In particular, it is concerned with amino acid derivatives of the formula

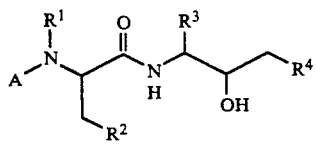

wherein $R^1$ is hydrogen or methyl, $R^2$ is ethyl, propyl, isopropyl, imidazol-2-yl, imidazol-4-yl, pyrazol-3-yl, thiazol-4-yl, thien-2-yl, ethoxycarbonyl, t-butylcarbonylmethyl, benzyloxycarbonylmethyl or t-butoxy, $R^3$ is isobutyl, cyclohexylmethyl or benzyl. $R^4$ is nitro, amino or a group of the formula $-N(R^5)(R^6)$ and A is one of the groups

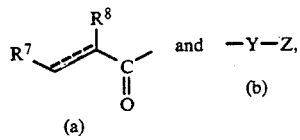

wherein $R^5$ is alkyl, alkoxyalkyl or optionally substituted phenyl, phenylalkyl or phenylsulfonylalkyl and $R^6$ is alkyl, alkoxyalkyl, optionally substituted phenyl, phenylalkyl or phenylsulfonylalkyl, alkanoyl, alkoxycarbonyl, arylalkoxycarbonyl, optionally substituted benzimidazolonyl or the residue of an optionally acylated amino acid or of an optionally acylated dipeptide or $R^5$ and $R^6$ together with the nitrogen atom to which they are attached are a 5- or 6-membered heterocycle, a 5- or 6-membered lactam or a 5- or 6-membered imide, with the proviso that A is not group (b) when $R^6$ is alkanoyl, alkoxycarbonyl or arylalkoxycarbonyl, the dotted line can be an additional bond, $R^7$ is phenyl, substituted phenyl, benzyl or naphthyl and R is hydrogen alkoxycarbonylalkyl, alkylcarbonylalkyl, cycloalkylcarbonylalkyl, heterocycloalkylcarbonylalkyl, arylcarbonylalkyl, aminocarbonylalkyl, substituted aminocarbonylalkyl, aminoalkylcarbonylalkyl, substituted aminoalkylcarbonylalkyl, aminoalkylsulfonylalkyl, substituted aminoalkylsulfonylalkyl, alkoxycarbonylhydroxyalkyl, alkylcarbonylhydroxyalkyl, cycloalkylcarbonylhydroxyalkyl, heterocycloalkylcarbonylhydroxyalkyl, arylcarbonylhydroxyalkyl, aminocarbonylhydroxyalkyl, substituted aminocarbonylhydroxyalkyl, dialkoxyphosphoroxyalkyl, diphenyloxyphosphoroxyalkyl, arylalkyl, alkoxycarbonylamino, arylalkoxycarbonylamino, alkylthioalkyl, alkylsulfinylalkyl, alkylsulfonylalkyl, arylthioalkyl, arylsulfinylalkyl, arylsulfonylalkyl, arylalkylthioalkyl, arylalkylsulfinylalkyl or arylalkylsulfonylalkyl, with the proviso that $R^8$ is not alkoxycarbonylamino or arylalkoxycarbonylamino when $R^7$ is phenyl, benzyl or α-naphthyl, Y is the bivalent residue of optionally N- and/or α-methylated phenylglycine, cyclohexylglycine, phenylalanine, cyclohexylalanine, 4-fluorophenylalanine, 4-chlorophenylalanine, tyrosine, O-methyltyrosine, α-naphthylalanine or homophenylalanine linked with Z at the N-terminal and Z is hydrogen or acyl, in the form of optically pure diastereomers, mixtures of diastereomers, diastereomeric racemates or mixtures of diastereomeric racemates as well as pharmaceutically usable salts of these compounds.

These novel compounds have pharmacodynamic properties which are useful in the treatment and control of high blood pressure and cardiac insufficiency.

Objects of the present invention are the compounds of formula I and their pharmaceutically usable salts per se and for use as therapeutically active substances, the preparation of these compounds, medicaments containing these and the preparation of such medicaments, as well as the use of compounds of formula I and their pharmaceutically usable salts in the control or prevention of illnesses or in the improvement of health, especially in the control or prevention of high blood pressure and cardiac insufficiency.

The following definitions of the general terms used in the present description apply irrespective of whether the terms in question appear alone or in combination with other chemical terms.

The term "alkyl" used in the present description is a straight-chain or branched, saturated hydrocarbon residue with 1-8, preferably 1-4, carbon atoms such as methyl, ethyl, n-propyl, isopropyl, n-butyl, isobutyl, sec.-butyl, t-butyl, pentyl, hexyl and the like. The term "alkoxy" is an alkyl ether group in which the term "alkyl" has the above significance, such as methoxy, ethoxy, propoxy, isopropoxy, butoxy, isobutoxy, sec.-butoxy, t-butoxy and the like. The term "cycloalkyl" is a saturated, cyclic hydrocarbon residue with 3-8, preferably 3-6, carbon atoms such as cyclopropyl, cyclobutyl, cyclopentyl, cyclohexyl and the like. The term "heterocycloalkyl" relates in the same manner to saturated, 3-8-membered, preferably 5- or 6-membered, cyclic hydrocarbon residues in which one or two methylene groups is/are replaced by one or two oxygen, sulfur or optionally alkyl-, phenylalkyl-. alkanoyl- or alkanoyloxy-substituted nitrogen atoms, such as piperidinyl, pyrazinyl, N-benzylpyrazinyl, morpholinyl, N-methylpiperidinyl, N-benzylmorpholinyl and the like. The term "alkanoyl" is the acid residue of a straight-chain or branched alkanoic acid with 1-8, preferably 1-4, carbon atoms such as formyl, acetyl, propionyl, butyryl, valeryl, isovaleryl and the like. The term "aryl" denotes a mono- or bicyclic aromatic hydrocarbon residue with 6-14 carbon atoms which is optionally mono- or multiply-substituted by alkyl, alkoxy, alkanoyloxy, amino, alkylamino, dialkylamino, alkylcarbonylamino, hydroxy, halogen, trifluoromethyl or nitro, such as phenyl, α- or β-naphthyl, indenyl, anthryl or phenanthryl and the like. The term "arylalkyl" denotes straight-chain or branched alkyl groups in which one or more hydrogen atoms is/are replaced by aryl groups, such as benzyl, diphenylmethyl, trityl, α- or β-naphthylmethyl, 2-phenylethyl, 3-phenyl-2-propyl 4-phenyl-3-butyl 2-(α- or β-naphthyl)ethyl, 3-α-naphthyl-2-propyl, 4-α-naphthyl 3-butyl and the like, whereby the aromatic residue can in each case be mono- or multiply-substituted as indicated above. The term "substituted phenyl" denotes phenyl optionally mono- or multiply-substituted by alkyl, alkoxy, alkoxyalkoxy, alkanoyl, alkanoyloxy, hydroxy, halogen or trifluoromethyl, such as 4-hydroxyphenyl, 4-methoxyphenyl, 4-methylphenyl, 4-chlorophenyl, 4-ethoxyethoxyphenyl and the like. Examples of optionally substituted benzimidazolonyl are benzimidazolonyl, 3-methylbenzimidazolonyl, 3-isopropylbenzimidazolonyl 3-butylbenzimidazolonyl, 3-morpholinoethylbenzimidazolonyl, 3-benzylbenzimidazonyl and the like. The term "5- or 6-membered heterocycle" relates to saturated 5- or 6-membered heterocycles having at least one nitrogen atom and optionally an additional oxygen, nitrogen or sulfur atom as the ring member(s) such as piperidinyl, pyrazinyl, morpholinyl, thiomorpholinyl, pyrrolidinyl, thiazolidinyl, imidazolidinyl, oxazolidinyl and the like. The term "5- or 6-membered lactam" relates to cyclic amides of saturated or branched alkanoic acids. The term "5- or 6-membered imide" relates in the same manner to cyclic diamides of dibasic acids such as succinic acid, glutaric acid, phthalic acid and the like.

The term "substituted amino" is an amino group which is mono- or di-substituted by alkyl, arylalkyl, alkanoyl, alkoxycarbonyl or arylalkoxycarbonyl or disubstituted by $C_3-C_6$-alkylene which is optionally interrupted by an oxygen, sulfur or optionally alkyl-, phenylalkyl-, alkanoyl or alkanoyloxy-substituted nitrogen atom. The term "acyl" relates to the acyl group of a carboxylic acid, an optionally N-substituted carbamic or thiocarbamic acid, an optionally N-substituted oxalamide, a sulfonic acid or an optionally N-substituted amidosulfonic acid, especially those with the partial formulas $R^b$—CO—, $R^a$—O—CO—, $(R^b)(R^b)N$—CO—, $(R^b)(R^b)N$—CS—, $(R^b)(R^b)N$—CO—CO—, $R^b$—$SO_2$— or $(R^b)(R^b)N$—$SO_2$—, in which $R^a$ is an unsubstituted or substituted, saturated or unsaturated, aliphatic, cycloaliphatic, cycloaliphatic-aliphatic hydrocarbon residue with up to 18, preferably 10, carbon atoms which is optionally functionalized with amino, monoalkylamino, dialkylamino, alkanoylamino or alkanoyloxyamino, an unsubstituted or substituted aromatic, heteroaromatic, aromatic-aliphatic or heteroaromatic-aliphatic hydrocarbon residue with up to 18, preferably 10, carbon atoms or an unsubstituted or substituted, saturated 5- or 6-membered heterocyclic residue and $R^b$ is hydrogen or has the significance of $R^a$. The term "acyl" also relates to the monovalent residue of an optionally acylated amino acid or an optionally acylated dipeptide attached via the carboxyl group.

An unsubstituted or substituted, saturated or unsaturated, aliphatic, cycloaliphatic or cycloaliphatic-aliphatic hydrocarbon residue $R^a$ or $R^b$ is, for example, unsubstituted or substituted alkyl, alkenyl, alkynyl, mono-, bi- or tricycloalkyl, monocycloalkenyl, bicycloalkenyl, cycloalkylalkyl, cycloalkylalkenyl or cycloalkenylalkyl. "Substituted alkyl" is an alkyl residue in which one or more hydrogen atoms can be substituted by hydroxy, alkoxy, aryloxy, alkanoyloxy, halogen, hydroxysulfonyloxy, carboxy, alkoxycarbonyl, carbamoyl, alkylcarbamoyl, dialkylcarbamoyl, cyano, phosphono, esterified phosphono, amino or oxo, whereby the substituents are present in the 1-position of the alkyl residue only when this is attached to the carbonyl group in the partial formula $R^b$—CO—.

Examples of substituted alkyl are 2-hydroxyethyl, methoxymethyl, 2-methoxyethyl, phenoxymethyl, α- or β-naphthoxymethyl, acetoxymethyl, 2-acetoxyethyl, chloromethyl, bromomethyl, 2-chloro- or 2-bromoethyl, hydroxysulfonyloxymethyl, 2-hydroxysulfonyloxyethyl, carboxymethyl, 2-carboxyethyl, methoxycarbonylmethyl, 2-methoxycarbonylethyl, ethoxycarbonylmethyl, 2-ethoxycarbonylethyl, carbamoylmethyl, 2-carbamoylethyl, methylcarbamoylmethyl, dimethylcarbamoylmethyl, cyanomethyl, 2-cyanoethyl, 2-oxopropyl, 2-oxobutyl, hydroxycarboxymethyl, 1-hydroxy-2-carboxyethyl, hydroxyethoxycarbonylethyl, hydroxymethoxycarbonylethyl, acetoxymethoxycarbonylmethyl, 1,2-dihydroxy-2-carboxyethyl, 1,2-dihydroxy-2-ethoxycarbonylethyl, 1,2-dihydroxy-2-methoxycarbonylethyl, 1,2-diacetoxy-2-ethoxycarbonylethyl, 1,2-diacetoxy-2-methoxycarbonylethyl, 1-α-naphthoxy-3-carboxypropyl, 1-α-naphthoxy-2-ethoxycarbonylethyl, 1-α-naphthoxy-3-t-butoxycarbonylpropyl, 1-α-naphthoxy-2-benzyloxycarbonylethyl, 1-α-naphthoxy-3-carbamoylpropyl, α-naphthoxycyanomethyl, 1-α-naphthoxy-3-cyanopropyl, 1-α-naphthoxy-4-dimethylaminobutyl or 1-α-naphthoxy-3-oxobutyl.

The term "alkenyl" relates to straight-chain or branched, unsaturated hydrocarbon residues with 2–8, preferably 2–4, carbon atoms, whereby the double bond can be present in the 1-position of the alkenyl residue only when this is attached to the carbonyl group in the partial formula $R^b$—CO—. Vinyl, allyl, 2-butenyl or 3-butenyl are examples of such alkenyl residues. The alkenyl residues can be substituted by the same substituents as the alkyl residues.

The term "alkynyl" relates to hydrocarbon residues with 2–8, preferably 2–4, carbon atoms, which contain a triple bond, such as ethynyl, 1-propynyl or 2-propynyl. The term "bicycloalkyl" relates to bicyclic saturated hydrocarbon residues with 5–10, preferably 6–9, carbon atoms such as bicyclo[3.1.0]hex-1-yl, bicyclo[3.1.0]hex-2-yl, bicyclo[3 1.0]hex-3-yl, bicyclo[4.1 0]hept-1-yl, bicyclo[4.1.0]hept-4-yl, bicyclo[2.2.1]hept-2-yl, bicyclo[3.2.1]oct-2-yl, bicyclo[3.3.0]oct-3-yl, bicyclo[3.3.1]non-9-yl, α- or β-decahydronaphthyl and the like.

The term "tricycloalkyl" relates to a tricyclic saturated hydrocarbon residue with 8–10 carbon atoms, such as 1-adamantyl.

The term "cycloalkenyl" relates to an unsaturated cyclic hydrocarbon residue with 3–8, preferably 3–6, carbon atoms such as 1-cyclohexenyl, 1,4-cyclohexadienyl and the like.

The term "bicycloalkenyl" relates to a bicyclic unsaturated hydrocarbon residue with 5–10, preferably 7–10, carbon atoms such as 5-norbornen-2-yl, bicyclo[2.2.2]octen-2-yl, hexahydro-4,7-methanoind-1-en-6-yl and the like.

Cyclopropylmethyl, cyclobutymethyl, cyclopentylmethyl, cyclohexylmethyl and the like are examples of cycloalkylalkyl. Cyclohexylvinyl and cyclohexylallyl and the like can be named as examples of cycloalkylalkenyl. 1-Cyclohexenylmethyl, 1,4-cyclohexadienylmethyl and the like are examples of cycloalkenylalkyl.

The mentioned cycloaliphatic and cycloaliphatic-aliphatic residues can be substituted by the same substituents as alkyl.

An optionally substituted aromatic or aromatic-aliphatic hydrocarbon residue is, for example, unsubstituted or substituted aryl, arylalkyl or arylalkenyl. Styryl, 3-phenylallyl, 2-(α-naphthyl)vinyl, 2-(β-naphthyl)vinyl and the like are examples of arylalkenyl.

In an heteroaromatic or heteroaromatic-aliphatic hydrocarbon residue the heterocycle is mono-, bi- or tricyclic and contains one or two nitrogen atoms and/or an oxygen or sulfur atom and is linked with the group —CO—, —O—CO—, >N—CO—, >N—CS—, >N—CO—CO—, $SO_2$ or >N—$SO_2$- with one of its ring carbon atoms. Examples of such heteroaromatic hydrocarbon residues are pyrrolyl, furyl, thienyl, imidazolyl, pyrazolyl, oxazolyl, thiazolyl, pyridyl, pyrazinyl, pyrimidinyl, indolyl, quinolyl, isoquinolyl, quinoxalinyl, β-carbolinyl or a benz-fused, cyclopenta-, cyclohexa- or cyclohepta-fused derivative of these residues. The heteroaromatic residue can be substituted on a nitrogen atom by alkyl, phenyl or phenylalkyl, for example benzyl, and/or on one or more carbon atoms by alkyl, phenyl, phenylalkyl, halogen, hydroxy, alkoxy, phenylalkoxy or oxo and can be partially saturated. Examples of such heteroaromatic residues are 2- or 3-pyrrolyl, phenylpyrrolyl, for example 4- or 5-phenyl-2-pyrrolyl, 2-furyl, 2-thienyl, 2-imidazolyl, 2-, 3- or 4-pyridyl, 2-, 3- or 4-indolyl, substituted 2-indolyl, for example 1-methyl-, 5-methyl-, 5-methoxy-, 5-benzyloxy-, 5-chloro- or 4,5-dimethyl-2-indolyl, 1-benzyl-2-indolyl, 1-benzyl-3-indolyl, 4,5,6,7-tetrahydro-2-indolyl, cyclohepta[b]-5-pyrrolyl, 2-, 3- or 4-quinolyl, 4-hydroxy-2-quinolyl, 1-, 3- or 4-isoquinolyl, 1-oxo-1,2-dihydro-3-isoquinolyl, 2-quinoxalinyl, 2-benzofuranyl, 2-benzoxazolyl, 2-benzthiazolyl, benz[e]indol-2-yl, β-carbolin-3-yl and the like.

Examples of heteroaromatic-aliphatic hydrocarbon residues are 2- or 3-pyrrolylmethyl, 2-, 3- or 4-pyridylmethyl, 2-(2-, 3- or 4-pyridyl)ethyl, 4-imidazolylmethyl, 2-(4-imidazolyl)ethyl, 2-indolylmethyl, 3-indolylmethyl, 2-(3-indolyl)ethyl, 2-quinolylmethyl and the like.

A saturated 5- or 6-membered heterocyclic residue has at least one carbon atom, 1–3 nitrogen atoms and optionally one oxygen or sulfur atom as the ring member(s) and is linked with the group —CO— or -O—CO—, >N—CO—, N—CS—, >N—CO—CO—, —$SO_2$— or >N—$SO_2$— with one of its ring carbon atoms. The heterocycle can be substituted on one of its carbon atoms or on a ring nitrogen atom by alkyl, for example methyl or ethyl, phenyl or phenylalkyl, for example benzyl, or on one of its carbon atoms by hydroxy or oxo and/or can be benz-fused on two adjacent carbon atoms. Examples of such residues are pyrrolidin-3-yl, 4-hydroxypyrrolidin-2-yl, 5-oxopyrrolidin-2-yl, piperidin-2-yl, piperidin-3-yl, 1-methylpiperidin-2-yl, 1-methylpiperidin-3-yl, 1-methylpiperidin-4-yl, morpholin-2-yl, morpholin-3-yl, thiomorpholin-2-yl, thiomorpholin-3-yl, 1,4-dimethylpiperazin-2-yl, 2-indolinyl, 3-indolinyl, 1,2,3,4-tetrahydroquinol-2-, -3- or -4-yl, 1,2,3,4-tetrahydroisoquinol-1-, -3- or -4-yl, 1-oxo-1,2,3,4-tetrahydroisoquinol-3-yl and the like.

As residues of an amino acid attached via the carboxyl group there come into consideration natural α-amino acids having the L-configuration, homologues of such amino acids, for example in which the amino acid side-chain is lengthened or shortened by one or two methylene groups and/or in which a methyl group is replaced by hydrogen, substituted aromatic α-amino acids, for example substituted phenylalanine or phenylglycine in which the substituent can be alkyl, for example methyl, halogen, for example fluorine, chlorine, bromine or iodine, hydroxy, alkoxy, for example methoxy, alkanoyloxy, for example acetoxy, amino, alkylamino, for example methylamino, dialkylamino, for example dimethylamino, alkanoylamino, for example acetylamino or pivaloylamino, alkoxycarbonylamino, for example t-butoxycarbonylamino, arylmethoxycarbonylamino, for example benzyloxycarbionylamino, and/or nitro and can be present singly or multiply, benz-fused phenylalanine or phenylglycine such as α-naphthylalanine or hydrogenated phenylalanine or phenylglycine such as cyclohexylalanine or cyclohexylglycine, a 5- or 6-membered cyclic benzfused α-amino acid, for example indoline-2-carboxylic acid or 1,2,3,4-tetrahydroisoquinoline-3-carboxylic acid, a natural or homologous α-amino acid in which a carboxy group in the side-chain is present in esterified or amidated form, for example as an alkyl ester group such as methoxycarbonyl or t-butoxycarbonyl or as a carbamoyl group, as an alkylcarbamoyl group such as methylcarbamoyl or as a dialkylcarbamoyl group such as dimethylcarbamoyl, in which an amino group of the side-chain is present in acylated form, for example as an alkanoylamino group such as acetylamino or pivaloylamino, as an alkoxycarbonylamino group such as t-butoxycarbonylamino or as arylmethoxycarbonylamino group such as benzyloxycarbonylamino, or in which a hydroxy group of the side-chain is present in etherified or esterified form, for example as an alkoxy group such as methoxy, as an arylalkoxy group such as benzyloxy or as a lower alkanoyloxy group such as acetoxy, or epimers of such amino acids, that is, with the unnatural D-configuration. Examples of such amino acids are glycine, alanine, valine, norvaline, leucine, isoleucine, norleucine, serine, homoserine, threonine, methionine, cysteine, proline, trans-3- and trans-4-hydroxyproline, phenylalanine, tyrosine, 4-nitrophenylalanine, 4-aminophenylalanine, 4-chlorophenylalanine, β-phenylserine, phenylglycine, α-naphthylalanine, cyclohexylalanine, cyclohexylglycine, tryptophane, indoline-2-carboxylic acid, 1,2,3,4-tetrahydroisoquinoline-3-carboxylic acid, aspartic acid, asparagine, aminomalonic acid, aminomalonic acid monoamide, glutamic acid, glutamic acid mono-t-butyl ester, glutamine, N-dimethylglutamine, histidine, arginine, lysine, N-t-butoxycarbonyllysine, δ-hydroxylysine, ornithine, N-pivaloylornithine, α,γ-diaminobutyric acid or α,β-diaminopropionic acid and the like. The residue of the amino acid attached via the carboxyl group can be substituted N-terminally by alkyl, for example methyl or ethyl, in order to increase the stability of the compound of formula I against enzymatic degradation.

The residue of a dipeptide attached via the carboxyl group consists of two of the above-mentioned amino acids.

The term "acylated amino acid" or "acylated dipeptide" relates to one of the above-mentioned amino acids or a dipeptide from two of the above-mentioned amino acids which is substituted N-terminally by the acyl residue of a carboxylic acid, of a half ester of carbonic acid, of an optionally N-substituted carbamic or thiocarbamic acid, of an optionally N-substituted oxalamide, of a sulfonic acid or of an optionally N-substituted amidosulfonic acid.

The term "pharmaceutically usable salts" embraces salts with inorganic or organic acids such as hydrochloric acid, hydrobromic acid, nitric acid, sulfuric acid, phosphoric acid, citric acid, formic acid, maleic acid, acetic acid, succinic acid, tartaric acid, methanesulfonic acid, p-toluenesulfonic acid and the like. Such salts can be prepared readily by any person skilled in the art having regard to the state of the art and taking into consideration the nature of the compound to be converted into a salt.

The compounds of formula I have at least three asymmetric carbon atoms and are therefore present in the form of optically pure diastereomers, mixtures of diastereomers, diastereomeric racemates or mixtures of diastereomeric racemates. The present invention embraces all forms. Mixtures of diastereomers, diastereomeric racemates or mixtures of diastereomeric racemates can be separated according to usual methods, for example by column chromatography thin-layer chromatography, HPLC and the like.

Those compounds of formula I in which $R^1$ is hydrogen are preferred. $R^2$ preferably is imidazol-2-yl, imidazol-4-yl or thiazol-4-yl, particularly imidazol-4-yl. Further, those compounds of formula I in which $R^3$ is cyclohexylmethyl are preferred $R^4$ preferably is —$N(R^5)(R^6)$ Preferably, $R^5$ is alkyl, particularly methyl, and $R^6$ is the residue of an optionally acylated amino acid or of an optionally acylated dipeptide, particularly the acylated residue of histidine or phenylalanine or the acylated residue of the dipeptide from histidine and phenylalanine, or $R^5$ and $R^6$ together with the nitrogen atom to which they are attached are a 5- or 6-membered lactam. The compounds of formula I in which A is group (a) are also preferred. $R^7$ preferably is phenyl or substituted phenyl, particularly phenyl. The preferred significance of $R^8$ is alkylcarbonylalkyl, aminoalkylcarbonylalkyl, substituted aminoalkylcarbonylalkyl, aminoalkylsulfonylalkyl, substituted aminoalkylsulfonylalkyl or alkylsulfonylalkyl, preferably alkylcarbonylalkyl or alkylsulfonylalkyl, particularly $C_1$-$C_4$-alkylcarbonylmethyl or $C_1$-$C_4$-alkylsulfonylmethyl. Where A is group (b), then there are preferred those compounds of formula I in which Y is the bivalent residue of phenylalanine linked with Z at the N-terminal. Z preferably is the group $R^a$—O—CO— in which $R^a$ is an optionally substituted, saturated aliphatic hydrocarbon residue with up to 10 carbon atoms or an optionally substituted heteroaromatic hydrocarbon residue with up to 18 carbon atoms, quite particularly the group $R^a$—O—CO— in which $R^a$ is a saturated, aliphatic hydrocarbon residue with up to 6 carbon atoms or a heteroaromatic residue with up to 10 carbon atoms.

From the above it follows that there are quite particularly preferred those compounds of formula I in which $R^1$ is hydrogen, $R^2$ is imidazol-4-yl, $R^3$ is cyclohexylmethyl, $R^4$ is —$N(R^5)(R^6)$, $R^5$ is methyl, $R^6$ acylated residue of histidine or phenylalanine or the acylated residue of the dipeptide from histidine and phenylalanine. $R^7$ is phenyl and $R^8$ is $C_1$-$C_4$-alkylcarbonylmethyl or $C_1$-$C_4$-alkylsulfonylmethyl.

Quite especially preferred compounds of formula I are:

(S)-N-[(1S,2S)-1-(Cyclohexylmethyl)-2-hydroxy-3-(2-oxopiperidino)propyl]-α-[(R)-α-(3,3-dimethyl-2-oxobutyl)hydrocinnamamido]imidazole-4-propionamide, (S)-N [(1S,2S)-1-(cyclohexylmethyl)-3-[(S)-α-[(R)-α-(3,3-dimethyl-2-oxobutyl)hydrocinnamamido]-N-isopropylimidazol-4-propionamido]-2-hydroxypropyl]-α-[(R)-α-(3,3-dimethyl-2-oxobutyl)hydrocinnamamido]imidazole-4-propionamide, (S)-N-[(1S,2S)-1-(cyclohexylmethyl)-2-hydroxy-3-[[(S)-1-[(S)-α-(3,3-dimethyl-2-oxobutyl)hydrocinnamamido]-2-imidazol-4-yl-ethyl]methylamino]-propyl]-α-[(R)-α-(3,3-dimethyl-2-oxobutyl)hydrocinnamamido]imidazole-4-propionamide.

(S)-N-[(1S,2S)-1-(cyclohexylmethyl)-2-hydroxy-3-[(S)-3-(imidazol-4-yl)-2-hydrocinnamamido-N-methylpropionamido]propyl]-α-[(R)-α-(3,3-dimethyl-2-oxobutyl)hydrocinnamamido]imidazole-4-propionamide.

t-butyl [(S)-α-[[(S)-1-[[(1S,2S)-3-[[(S)-1-[(S)-α-(1--t-butoxyformamido)hydrocinnamamido]-2-imidazol-4-ylethyl]methylcarbamoyl]-1-(cyclohexylmethyl)-2-hydroxypropyl]carbamoyl]-2-imidazol-4-ylethyl]carbamoyl]phenethyl]carbamate, t-butyl [(S)-α-[[(2S,3S)-3-[(S)-2-[(S)-α-(1-t-butoxyformamido)hydrocinnamamido]-3-imidazol-4-ylpropionamido]-4-cyclohexyl-2-hydroxybutyl]methylcarbamoyl]phenethyl]carbamate and (S)-N-[(1S.2S)-1-(cyclohexylmethyl)-2-hydroxy-3-phthalimidopropyl]-α-[(R)-α-(3,3-dimethyl-2-oxobutyl)hydrocinnamamido]imidazole-4-propionamide.

The compounds of formula I in the form of optically pure diastereomers, mixtures of diastereomers, diastereomeric racemates or mixtures of diastereomeric racemates as well as pharmaceutically usable salts thereof can be prepared by a) reacting a compound of the formula

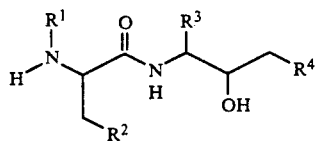

II wherein R¹, R², R³ and R⁴ have the significance given above, with an acylating agent yielding the group

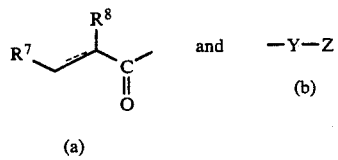

wherein R⁷, R⁸, Y, Z and the dotted line have the significance given above, or b) reacting a compound of the formula

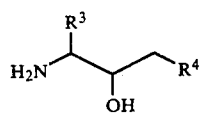

III wherein R³ and R⁴ have the significance given above, with a compound of the formula

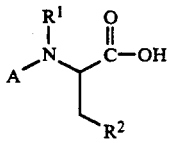

IV wherein R¹, R² and A have the significance given above, or an activated derivative thereof, or c) reacting a compound of formula I in which Z is hydrogen and the remaining symbols have the significance given above with an optionally acylated amino acid or an optionally acylated dipeptide, or d) for the preparation of a compound of formula I in which A contains a free amino group and/or R⁴ is amino and/or R² is imidazol-2-yl, imidazol-4-yl or pyrazol-3-yl, cleaving off the N-protecting group(s) from a corresponding compound of formula I in which A contains a N-protected amino group and/or from a compound corresponding to formula I but in which R⁴ is N-protected amino and/or R² is N-protected imidazol-2-yl, imidazol-4-yl or pyrazol-3-yl, or e) for the preparation of a compound of formula I in which R⁴ is a 5- or 6-membered imide, reacting a corresponding compound of formula I in which R⁴ is amino with an anhydride of a dibasic acid, or f) for the preparation of a compound of formula I in which R⁵ is alkyl, alkoxyalkyl or optionally substituted phenyl, phenylalkyl or phenylsulfonylalkyl and R⁶ is alkyl, alkoxyalkyl, optionally substituted phenyl, phenylalkyl or phenylsulfonylalkyl, alkanoyl, alkoxycarbonyl, arylalkoxycarbonyl or the residue of an optionally acylated amino acid or of an optionally acylated dipeptide, reacting a compound corresponding to formula I but in which R⁶ is hydrogen and R⁵ is alkyl, alkoxyalkyl or optionally substituted phenyl, phenylalkyl or phenylsulfonylalkyl with an acylating agent yielding the residue R⁶, and g) if desired, separating a mixture of diastereomeric racemates into the diastereomeric racemates or optically pure diastereomers, and/or h) if desired, separating a mixture of diastereomers into the optically pure diastereomers, and/or i) if desired, converting a compound obtained into a pharmaceutically usable salt.

The acylation of a compound of formula II is effected according to methods known per se. Especially suitable acylating agents are activated acid derivatives such as esters, mixed esters, acid halides and acid anhydrides or mixed acid anhydrides. The reaction is carried out in an organic solvent or solvent mixture which is inert under the reaction conditions at a temperature between about 0° C. and room temperature. As solvents there come into consideration especially aromatic hydrocarbons such as benzene, toluene or xylene, chlorinated hydrocarbons such as methylene chloride or chloroform, ethers such as diethyl ether, tetrahydrofuran or dioxan, and the like. Where the acylating agent is a peptide, the reaction is effected under reaction conditions which are usual in peptide chemistry, that is, preferably in the presence of a condensation agent such as HBTU (O-benzotriazolylo N,N,N',N'-tetramethyluronium hexafluorophosphate), BOP (benzotriazol-1-yloxy-bis-(dimethylamino)phosphonium hexafluorophosphate), BOPC (bis(2-oxo-2-oxozolidinyl)phosphine chloride), HOBT (N-hydroxybenzotriazole), DBU (1,8-diazabicyclo[5.4.0]undec-7-ene), DCC (dicyclohexylcarbodiimide), EDC (N-ethyl-N'(3-dimethylaminopropyl)carbodiimide hydrochloride), Hünig base (ethyldiisopropylamine), and the like. The reaction is conveniently carried out in an organic solvent or solvent mixture which is inert under the reaction conditions at a temperature between about 0° C. and 50° C., preferably at about room temperature. As solvents there come into consideration especially dimethylformamide, methylene chloride, acetonitrile, tetrahydrofuran, and the like.

The reaction of a compound of formula III with a compound of formula IV is also effected according to methods which are known per se in peptide chemistry, that is, under the same conditions as have been given above for the reaction of a compound of formula II with a peptide. Examples of suitable activated derivatives of a compound of formula IV are acid halides, acid anhydrides, mixed anhydrides, esters, mixed esters, and the like.

The reaction of a compound of formula I in which Z is hydrogen with an optionally acylated amino acid or an optionally acylated dipeptide in accordance with process variant c) is also effected according to methods which are known per se in peptide chemistry, that is, under the conditions given above for the reaction of a compound of formula II with a peptide.

The cleavage of the N-protecting group(s) in accordance with process variant d) is also effected according to methods known per se depending on the nature of the N-protecting group to be cleaved off. However, the cleavage is conveniently effected by acidic or basic hydrolysis. For the acidic hydrolysis there is advantageously used a solution of a mineral acid such as hydrochloric acid, hydrobromic acid, trifluoroacetic acid, sulfuric acid, phosphoric acid and the like in an inert solvent or solvent mixture. Suitable solvents are alcohols such as methanol or ethanol, ethers such as tetrahydrofuran or dioxan, chlorinated hydrocarbons such as methylene chloride, and the like. For the basic hydrolysis there can be used alkali metal hydroxides and carbonates such as potassium or sodium hydroxide or potassium or sodium carbonate, organic amines such as piperidine, and the like. Inert organic solvents such as are named above for the acidic hydrolysis can be added as solubilizers. The reaction temperature for the acidic and basic hydrolysis can be varied in a range of about 0° C. to the reflux temperature, with the reaction being preferably carried out between about 0° C. and room temperature. The t-butoxycarbonyl residue is conveniently cleaved off with trifluoroacetic acid or formic acid in the presence or absence of an inert solvent. The Fmoc protecting group is conveniently cleaved off with piperidine at about room temperature. The benzyloxycarbonyl group can be cleaved off in a known manner by acidic hydrolysis as described above or hydrogenolytically.

The reaction of a compound of formula I in which $R^4$ is amino with an anhydride of a dibasic acid is also effected according to methods known per se in an organic solvent which is inert under the reaction conditions at a temperature between about room temperature and the reflux temperature. Suitable solvents are aromatic hydrocarbons such as toluene or xylene, acetonitrile, dimethylformamide and the like.

The acylation of a compound corresponding to formula I but in which $R^6$ is hydrogen and $R^5$ is alkyl, alkoxyalkyl or optionally substituted phenyl, phenylalkyl or phenylsulfonylalkyl with an acylating agent yielding the residue $R^6$ is also effected according to methods known per se. Suitable acylating agents are acid halides, acid anhydrides, mixed anhydrides, acid azides, esters, mixed esters and the like. The reaction is effected in an organic solvent or solvent mixture which is inert under the reaction conditions at a temperature between about room temperature and the reflux temperature of the reaction mixture, preferably at about room temperature. The reaction can be carried out in the presence or absence of an acid-binding agent such as sodium or potassium carbonate, pyridine, triethylamine and the like.

The starting materials of formula II are novel and are also an object of the present invention. These compounds can be prepared by reacting a compound of formula III with optionally N-methylated histidine, leucine, norleucine, norvaline, thiazolylalanine, thienylalanine, aspartic acid ethyl ester, glutamic acid t-butyl ester, glutamic acid benzyl ester or t-butoxyserine. This reaction is also effected according to methods which are known in peptide chemistry, that is, under the reaction conditions which are described above for the reaction of a compound of formula II with a dipeptide.

The starting materials of formula III are also novel and are an object of the present invention. They can be prepared, for example, by cleaving off the amino protecting group in a compound of the formula

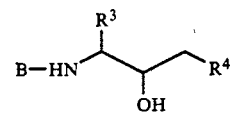

V wherein B is an amino protecting group, preferably t-butoxycarbonyl or benzyloxycarbonyl, and $R^3$ and $R^4$ have the significance given above.

The cleavage of the N-protecting group is also effected according to methods known per se, for example in an organic solvent or solvent mixture which is inert under the reaction conditions at a temperature between about 0° C. and room temperature with an acid such as hydrochloric acid, trifluoroacetic acid, and the like. Suitable solvents are ethers such as tetrahydrofuran or dioxan, alcohols such as methanol or chlorinated hydrocarbons such as methylene chloride, and the like.

The starting materials of formula IV are known or can be obtained in analogy to the preparation of the known compounds.

The compounds of formula V are also novel and are an object of the present invention. Those in which $R^4$ is amino or the group $-N(R^5)(R^6)$ can be prepared, for example, by reacting an amino compound of the formula

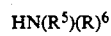

VI wherein $R^5$ and $R^6$ have the significance given above, with an epoxide of the formula

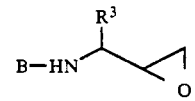

VII wherein B and $R^3$ have the significance given above.

The reaction of an amino compound of formula VI with an epoxide of formula VII is also effected according to methods known per se, for example in an organic solvent or solvent mixture which is inert under the reaction conditions at a temperature between about room temperature and the reflux temperature. Suitable solvents are alcohols such as methanol or ethanol, ethers such as diethyl ether, tetrahydrofuran or dioxan, and the like or mixtures thereof.

The compounds of formula V in which $R^4$ is nitro can also be prepared according to methods known per se, for example by reacting an aldehyde of the formula

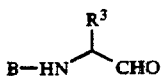

VIII wherein B and $R^3$ have the significance given above, with nitromethane in the presence of a strong base such as sodium hydride, sodium amide, potassium t-butylate and the like in an organic solvent which is inert under the reaction conditions, such as an ether, for example diethyl ether, tetrahydrofuran or dioxan, an alcohol, for example t-butyl alcohol, and the like at a temperature between about room temperature and the reflux temperature, preferably between about 30° and 50° C.

The compounds of formulas VI, VII and VIII are known or can be prepared in analogy to the preparation of the known compounds.

The compounds of formula I and their pharmaceutically usable salts have an inhibitory activity on the natural enzyme renin. The latter passes from the kidneys into the blood and there brings about the cleavage of angiotensinogen with the formation of the decapeptide angiotensin I which is then cleaved in the lungs, the kidneys and other organs to the octapeptide angiotensin II. Angiotensin II increases the blood pressure not only directly by arterial constriction, but also indirectly by the liberation of the sodium ion-retaining hormone aldosterone from the adrenal gland, with which is associated an increase in the extracellular fluid volume. This increase is attributed to the action of angiotensin II itself or to the heptapeptide angiotensin III which is formed therefrom as a cleavage product. Inhibition of the enzymatic activity of renin brings about a decrease in the formation of angiotensin I and as a consequence thereof the formation of a smaller amount of angiotensin II. The reduced concentration of this active peptide hormone is the actual reason for the blood pressure-lowering activity of renin inhibitors.

The activity of renin inhibitors can be demonstrated experimentally by means of the in vitro test described hereinafter:

In Vitro Test with Pure Human Renin

The test is carried out in Eppendorf test tubes. The incubation mixture consists of (1) 100 μl of human renin in buffer A (0.1M sodium phosphate solution, pH 7.4, 0.1% bovine serum albumin, 0.1% sodium azide and 1 mM ethylenediaminetetraacetic acid), sufficient for a renin activity of 2–3 ng of angiotensin I/ml/hr.; (2) 145 μl of buffer A; (3) 30 μl of 10 μm human tetradecapeptide renin substrate (hTD) in 10 mM hydrochloric acid; (4) 15 μl of dimethyl sulfoxide with or without inhibitor and (5) 10 μl of a 0.03 molar solution of hydroxy-quinoline sulfate in water.

The samples are incubated for three hours at 37° C. or 4° C. in triplicate. 2×100 μl samples per experimental test tube are used in order to measure the production of angiotensin I via RIA (standard radioimmunoassay; clininical assay solid phase kit). Cross reactivities of the antibody used in the RIA are: angiotensin I 100%; angiotensin II 0.0013%; hTD (angiotensin I-Val-Ile-His-Ser-OH) 0.09%. The production of angiotensin I is determined by the difference between the experiment at 37° C. and that at 4° C.

The following controls are carried out:

(a) Incubation of hTD samples without renin and without inhibitor at 37° C. and 4° C. The difference between these two values gives the base value of angiotensin I production.

(b) Incubation of hTD samples with renin, but without inhibitor at 37° C. and 4° C. The difference between these values gives the maximal value of angiotensin I production.

In each sample the base value of angiotensin I production is substracted from the angiotensin I production which is determined. The difference between the maximal value and the base value gives the value of the maximal substrate hydrolysis (=100%) by renin.

The results are given as $IC_{50}$ values which denote that concentration of the inhibitor at which the enzymatic activity is inhibited by 50%. The $IC_{50}$ values are determined from a linear regression curve from a logit-log plot.

The results obtained in this test are compiled in the following Table:

TABLE

| Compound | $IC_{50}$ value in μmol/lt. |
|---|---|
| A | 0.041 |
| B | 0.041 |
| C | 0.028 |
| D | 0.019 |
| E | 0.030 |
| F | 0.015 |
| G | 0.020 |

A = (S)-N-[(1S,2S)-1-(Cyclohexylmethyl)-2-hydroxy-3-(2oxopiperidino)propyl]-α-[(R)-α-(3,3-dimethyl-2-oxobutyl)hydrocinnamamido]imidazole-4-propionamide, B = (S)-N-[(1S,2S)-1-(Cyclohexylmethyl)-3-[(S)-α-[(R)-α-(3,3-dimethyl-2-oxobutyl)hydrocinnamamido]-N-isopropylimidazol-4-propionamido]-2-hydroxypropyl]-α-[(R)-α-(3,3-dimethyl-2-oxobutyl)hydrocinnamamido]imidazole-4-propionamide, C = (S)-N-[(1S,2S)-1-(Cyclohexylmethyl)-2-hydroxy-3-[[(S)-1-[(S)-α-(3,3-dimethyl-2-oxobutyl)-hydrocinnamamido]-2-imidazol-4-ylethyl]methylamino]propyl]-α-[(R)-α-(3,3-dimethyl-2-oxobutyl)hydrocinnamamido]imidazole-4-propionamide, D = (S)-N-[(1S,2S)-1-(Cyclohexylmethyl)-2-hydroxy-3-[(S)-3-(imidazol-4-yl)-2-hydrocinnamamido-N-methylpropionamido]propyl]-α-[(R)-α-(3,3-dimethyl-2-oxobutyl)hydrocinnamamido]imidazole-4-propionamide, E = t-Butyl [(S)-α-[[(S)-1-[[(1S,2S)-3-[[(S)-1-[(S)-α-(1-t-butoxyformamido)hydrocinnamamido]-2-imidazol-4-yl-ethyl]methylcarbamoyl]-1-(cyclohexylmethyl)-2-hydroxypropyl]carbamoyl]-2-imidazol-4-ylethyl]carbamoyl]phenethyl]carbamate, F=t-Butyl [(S)-α-[[(2S,3S)-3-[(S)-2-[(S)-α-(1-t-butoxyformamido)hydrocinnamamido]-3-imidazol-4-ylpropionamido]-4-cyclohexyl-2-hydroxybutyl]-methylcarbamoyl]phenethyl]carbamate and G=(S)-N-[(1S,2S)-1-(Cyclohexylmethyl)-2-hydroxy-3-phthalimidopropyl]-α-[(R)-α-(3,3-dimethyl-2-oxobutyl)hydrocinnamamido]imidazole-4-propionamide.

The compounds of formula I as well as their pharmaceutically usable salts can be used as medicaments, for example in the form of pharmaceutical preparations. The pharmaceutical preparations can be administered enterally such as orally, for example in the form of tablets, coated tablets, dragees, hard and soft gelatin capsules, solutions, emulsions or suspensions, nasally, for example in the form of nasal sprays, or rectally, for example in the form of suppositories. However, the administration can also be effected parenterally such as intramuscularly or intravenously, for example in the form of injection solutions.

For the preparation of tablets, coated tablets, dragees and hard gelatin capsules the compounds of formula I as well as their pharmaceutically usable salts can be processed with pharmaceutically inert, inorganic or organic excipients. Lactose, maize starch or derivatives thereof, talc, stearic acid or its salts etc can be used for example as such excipients for tablets, dragees and hard gelatin capsules.

Suitable excipients for soft gelatin capsules are for example vegetable oils, waxes, fats, semi-solid and liquid polyols etc.

Suitable excipients for the preparation of solutions and syrups are for example water, polyols, saccharose, invert sugar, glucose etc.

Suitable excipients for injection solutions are for example water, alcohols, polyols, glycerol, vegetable oils etc.

Suitable excipients for suppositories are for example natural or hardened oils, waxes, fats, semi-liquid or liquid polyols etc.

Moreover, the pharmaceutical preparations can contain preserving agents, solubilizers, viscosity-increasing substances, stabilizing agents, wetting agents, emulsifying agents, sweetening agents, colouring agents, flavouring agents, salts for varying the osmotic pressure, buffers, coating agents or antioxidants. They can also contain still other therapeutically valuable substances.

In accordance with the invention the compounds of formula I as well as their pharmaceutically usable salts can be used in the control or prevention of high blood pressure and cardiac insufficiency. The dosage can vary within wide limits and will, of course, be fitted to the individual requirements in each particular case. In general, in the case of oral administration there should suffice a daily dosage of about 3 mg to about 3 g, preferably about 10 mg to about 1 g, for example approximately 300 mg per person, divided in preferably 1-3 unit doses, which can for example be of the same amount, whereby, however, the upper limit just given can also be exceeded when this is found to be indicated. Usually, children receive half of the adult dosage.

The following Examples are intended to illustrate the present invention, but are not intended to be limiting in any manner. All temperatures are given in degrees Celsius. The following abbreviations are used:

H-His-OH = L-histidine

| | |
|---|---|
| H-Phe-OH = | L-phenylalanine |
| H-Phe-His-OH = | N-[(S)-2-amino-3-phenylpropyl]-L-histidine |
| Boc = | t-butoxycarbonyl |
| Fmoc = | 9-fluorenylmethoxycarbonyl |

EXAMPLE 1

63 mg (0.248 mmol) of α-[(S)-1-amino-2-cyclohexylethyl]-1-piperidineethanol (αR:αS=5:1) in 10 ml of acetonitrile were treated with 0.085 ml of Hünig base, 110 mg of BOP and 100 mg of Boc-Phe-His-OH. The solution obtained was subsequently stirred at room temperature for 12 hours. After the usual working-up the crude product, for purification, was chromatographed on silica gel with a 10:1 mixture of methylene chloride and methanol as the eluting agent, whereby there were obtained 50 mg (33%) of t-butyl [(S)-α-[[(S)-1-[[[1S,(2R:2S=5:1)]-1-(cyclohexylmethyl)-2-hydroxy-3-piperidinopropyl]carbamoyl]-2-imidazol-4-ylethyl]carbamoyl]phenethyl]carbamate as a resin, MS: 639 (M+H)+.

In an analogous manner, by reacting 183 mg (0.715 mmol) of (R:S=5:1)-α-[(S)-1-amino-2-cyclohexylethyl]morpholineethanol with 2.88 mg (0.715 mmol) of Boc-Phe-His-OH there were obtained 130 mg (28%) of t-butyl [(S)-α-[[(S)-1-[[(1S,2R:2S=5:1)-1-(cyclohexylmethyl)-2-hydroxy-3-morpholinopropyl]carbamoyl]-2-imidazol-4-ylethyl]carbamoyl]phenethyl]carbamate as a foam, MS: 641 (M+H)+.

The α-[(S)-1-amino-2-cyclohexylethyl]-1-piperidine ethanol (αR:αS=5:1) used as the starting material was prepared as follows:

600 mg (2.22 mmol) of t-butyl [(1S,2R:S=9:1)-1-(cyclohexylmethyl)-2,3-epoxypropyl]carbamate, prepared according to the method described by S. W. Rosenberg et al. in J. Med. Chem. 30, 1224 (1987) from t-butoxycarbonylamino-3(S)-cyclohexylpropylaldehyde [prepared, in turn, according to the method described by J. Boger et al. in J. Med. Chem., 28, 1779 (1985)], in 10 ml of ethanol were treated with 0.658 ml (6.7 mmol) of piperidine and the mixture obtained was subsequently heated to reflux for 12 hours. After cooling ether and water were added thereto, the two phases were separated, the organic phase was dried over sodium sulfate and the residue remaining after removal of the solvent under reduced pressure was chromatographed on silica gel with a 10:1 mixture of chloroform and methanol as the eluting agent. In this manner there were obtained 600 mg (76%) of t-butyl [(1S)-1-(cyclohexyl-methyl)-2-hydroxy-3-piperidinopropyl]carbamate (2R:2S=5:1) as a white solid, MS: 355 (M+H)+.

600 mg (1.69 mmol) of t-butyl [(1S)-1-(cyclohexylmethyl)-2-hydroxy-3-piperidinopropyl]carbamate were dissolved in 6 ml of 5.2N hydrochloric acid in dioxan and subsequently stirred at room temperature for 2 hours. Thereafter, the reaction solution was evaporated under reduced pressure, made alkaline with 25% ammonia solution and extracted with ether. Drying and evaporation of the ether extract yielded 400 mg (93%) of α-[(S)-1-amino-2-cyclohexylethyl]-1-piperidineethanol (αR:αS=5:1) as a resin, MS: 236 (M-H₂O)+.

In an analogous manner to that described above, by reacting 600 mg (2.22 mmol) of t-butyl [(1S,2R:S=9:1)-1-(cyclohexylmethyl)-2,3-epoxypropyl]carbamate with 0.4 ml (4.4 mmol) of morpholine there were obtained 700 mg (89%) of t-butyl [(1S,2R:2S=5:1)-1-(cyclohexylmethyl-2-hydroxy-3-morpholinopropyl]carbamate as an oil, MS: 338 (M-H$_2$O)$^+$, which, by stirring in 5.2N hydrochloric acid in dioxan, were converted into 465 mg (90%) of (R:S=5:1)-α-[(S)-1-amino-2-cyclohexylethyl]morpholine-ethanol in the form of an oil, MS: 156 (M-morpholinomethyl)$^+$.

EXAMPLE 2

58 mg (0.2 mmol) of α-[(S)-1-amino-2-cyclohexylethyl]-N-ethyl-N-phenylaminoethanol, obtained by cleaving off the Boc protecting group with 5N hydrochloric acid in dioxan from t-butyl [(1S.2R:S=5:1)-1-(cyclohexylmethyl)-2-hydroxy-3-(ethylphenylamino)-propyl]carbamate [prepared from t-butyl [(1S,2R:S=9:1)-1-(cyclohexylmethyl)-2,3-epoxypropyl]carbamate and N-ethylamidine in an analoqous manner to that described in Example 1], were dissolved in 5 ml of acetonitrile and treated with 42 ml of Hünig base, 91 mg of BOP and 100 mg of 1-(t-butoxycarbonyl)-N-[(R)-α-(3,3-dimethyl-2-oxobutyl)hydrocinnamoyl]-L-histidine. Subsequently, the reaction mixture obtained was stirred at room temperature for 12 hours and then evaporated under reduced pressure. The residue was partitioned between saturated sodium bicarbonate solution and ethyl acetate and the organic phase was separated, dried and evaporated. Chromatography of the residue on silica gel using a 20:1 mixture of methylene chloride and methanol as the eluting agent yielded 120 mg of a product which, for the cleavage of the Boc protecting group on the imidazole ring, was dissolved in methanol and, after the addition of a spatula tip of potassium carbonate, stirred at room temperature for 2 hours. After the usual working-up and chromatography of the residue on silica gel there were obtained 76 mg of (S)-N-[(1S,2R:2S=5:1)-1-(cyclohexylmethyl)-3-(ethylphenylamino)-2-hydroxypropyl]-α-[(R)-α-(3,3-dimethyl-2-oxobutyl)hydrocinnamamido]imidazole-4-propionamide as a resin, MS: 658 (M+H)$^+$.

The 1-(t-butoxycarbonyl)-N-[(R)-α-(3,3-dimethyl-2-oxobutyl)hydrocinnamoyl]-L-histidine used as the starting material was prepared as follows:

A suspension of 3.0 g (12 mmol) of (R)-α-(pivaloylmethyl)hydrocinnamic acid (see EPA 0,184,550) and 2.66 g (11 mmol) of L-histidine methyl ester dihydrochloride in 340 ml of dimethylformamide was treated at room temperature under a nitrogen atmosphere with 3.45 g (34 mmol) of triethylamine and 4.58 g (12 mmol) of HBTU. The reaction mixture was stirred at room temperature for 5 hours and subsequently evaporated in a high vacuum. The residue was dissolved in 500 ml of ethyl acetate and washed in succession with 100 ml of water, three times with 100 ml of saturated sodium bicarbonate solution each time and with 100 ml of saturated sodium chloride solution. The organic phase was dried over sodium sulfate, evaporated under reduced pressure and the yellowish crude product obtained was chromatographed on silica gel with a 95:5 mixture of methylene chloride and methanol which contained 0.1% ammonia. In this manner there were obtained 3.6 g of N-[(R)-α-(3,3-dimethyl-2-oxobutyl)hydrocinnamoyl]-L-histidine methyl ester as a colourless foam, MS: 399(M)$^+$.

A solution of 3.56 g (8.9 mmol) of N-[(R)-α-(3,3-dimethyl-2-oxobutyl)hydrocinnamoyl]-L-histidine methyl ester and 9.36 ml of 1N sodium hydroxide solution in 50 ml of methanol was stirred at room temperature for 15 hours and thereafter evaporated in the cold under reduced pressure. The residue was dissolved in 70 ml of dioxan and 30 ml of water, a solution of 2.95 (13.5 mmol) of di-t-butyl dicarbonate was added dropwise thereto at room temperature and the mixture was thereafter stirred at room temperature for 15 hours. For the working-up, the reaction solution was concentrated to about ⅓ of its volume under reduced pressure and then diluted with 200 ml of ethyl acetate. After the addition of 50 ml of ice-water the reaction mixture was adjusted to pH 2.5 and the aqueous phase was saturated with solid sodium chloride. The aqueous phase was extracted twice with ethyl acetate and the combined ethyl acetate phases were dried over sodium sulfate and evaporated. The crude product obtained was chromatographed on silica gel with a 95:5 mixture of methylene chloride and methanol which contained 0.1% acetic acid, whereby there were obtained 3.5 g of 1-(t-butoxy-carbonyl)-N-[(R)-α-(3,3-dimethyl-2-oxobutyl)hydrocinnamoyl]-L-histidine as a colourless powder, MS: 486 (M+H)$^+$.

EXAMPLE 3

3.45 g (5 mmol) of benzyl [(2S,3S)-4-cyclohexyl-3[(S)-α-[(R)-α-(3,3-dimethyl-2-oxobutyl)hydrocinnamamido]imidazole-4-propionamido]-2-hydroxybutyl]carbamate in 50 ml of methanol were treated with 0.57 g of pyridine hydrochloride and, after the addition of 0.5 g of palladium on charcoal (5%), hydrogenated for 4 hours. Thereafter, the catalyst was removed by filtration and the filtrate was evaporated under reduced pressure, whereby there were obtained 3.25 g of (S)-N-[(1S,2S)-3-amino-1-(cyclohexylmethyl)-2-hydroxypropyl]-α-[(R)-α-(3,3-dimethyl-2-oxo-butyl)hydrocinnamamido]imidazole-4propionamide hydrochloride as an amorphous solid, MS: 554 (M+H)$^+$.

The benzyl [(2S,3S)-4-cyclohexyl-3-[(S)-α-[(R)-α-(3,3-dimethyl-2-oxobutyl)hydrocinnamamido]imidazole-4propionamido]-2-hydroxybutyl]-carbamate used as the starting material was prepared as follows:

11.9 g (29.7 mmol) of t-butyl [(S)-3-amino-(S)-2-(t-butyldimethylsiloxy)-1-(cyclohexylmethyl)propyl]carbamate (see U.S. Pat. No. 4,599,198) were dissolved in 150 ml of dimethylformamide, treated with 6.6 ml of Hünig base and cooled to 5°. While stirring vigorously there were added dropwise at this temperature within 10 minutes 4.65 ml of benzyl chloroformate and the reaction mixture was subsequently stirred at room temperature for 1 hour. Thereafter, the reaction mixture was concentrated in a high vacuum, poured into water and extracted with methylene chloride. The methylene chloride extracts were dried over potassium carbonate and evaporated, and the residue was chromatographed on 150 g of silica gel with a mixture of methylene chloride and hexane as the eluting agent, whereby there were obtained 11.05 g of 3-benzyl 1-t-butyl [(1S,2S)-2-(t-butyldimethylsiloxy)-1-(cyclohexylmethyl)propyl]-dicarbamate as an oil.

8.2 g (19.5 mmol) of 3-benzyl 1-t-butyl [(1S.2S)-2-(t-butyldimethylsiloxy)-1-(cyclohexylmethyl)propyl]-dicarbamate were dissolved in 100 ml of methylene chloride, treated with 25 ml of 90% trifluoroacetic acid while cooling with ice and stirred at room temperature for 4.5 hours. The reaction mixture was thereafter poured into ice-water, made alkaline with sodium carbonate solution and extracted with methylene chloride. The methylene chloride extracts were dried over potassium carbonate and evaporated under reduced pressure.

Chromatography of the resulting residue on 100 g of silica gel with a mixture of methylene chloride and isopropanol as the eluting agent yielded 4.95 g of benzyl [(2S,3S)-3-amino-4-(cyclohexylmethyl)-2-hydroxybutyl]carbamate as an amorphous solid, MS: 321 (M+H)+.

Reaction of benzyl [(2S,3S)-3-amino-4-(cyclohexylmethyl)-2-hydroxybutyl]carbamate with 1-(t-butoxycarbonyl)-N-[(R)-α-(3,3-dimethyl-2-oxobutyl)hydrocinnamoyl]-L-histidine and cleavage of the Boc protecting group on the imidazole ring with potassium carbonate in methanol in an analogous manner to that described in Example 2 yielded benzyl [(2S,3S)-4-cyclohexyl-3-[(S)-α-[(R)-α-(3,3-dimethyl-2-oxobutyl)-hydrocinnamamido]imidazole-4-propionamido]-2-hydroxybutyl]carbamate as an amorphous solid, MS: 688 (M+H)+.

EXAMPLE 4

408 mg (0.565 mmol) of (S)-N-[(1S,2S)-1-(cyclohexylmethyl)-2-hydroxy-3-(2-oxo-1-pyrrolidinyl)propyl]-α-[(R)-α-(3,3-dimethyl-2-oxobutyl)hydrocinnamamido]-3-t-butoxycarbonylimidazole-4-propionamide were dissolved in 5.5 ml of methanol, treated with 23 mg of potassium carbonate and stirred at room temperature for 5 hours. Thereafter, the reaction mixture was poured into ice-water and extracted with methylene chloride. The methylene chloride extracts were dried over potassium carbonate and evaporated, and the residue was chromatographed on 35 g of silica gel with a mixture of methylene chloride and isopropanol as the eluting agent, whereby there were obtained 280 mg (80%) of (S)-N-[(1S,2S)-1-(cyclohexylmethyl)-2-hydroxy-3-(2-oxo-1-pyrrolidinyl)propyl]-α-[(R)-α-(3,3-dimethyl-2-oxobutyl)hydrocinnamamido]-imidazole-4-propionamide as an amorphous solid, MS: 622 (M+H)+.

The (S)-N-[(1S,2S)-1-(cyclohexylmethyl)-2-hydroxy-3o (2-oxo-1-pyrrolidinyl)propyl]-α-[(R)-α-(3,3-dimethyl2-oxobutyl)hydrocinnamamido]-3-t-butoxycarbonylimidazole-4-propionamide used as the starting material was prepared as follows:

1.6 g (4.0 mmol) of t-butyl [(S)-3-amino-(S)-2-(t-butyldimethylsiloxy)-1-(cyclohexylmethyl)propyl]carbamate were dissolved in 20 ml of dimethylformamide and treated at room temperature with 1.12 ml of triethylamine and 0.68 ml of ethyl 4-bromobutyrate. The reaction mixture was thereafter stirred at 95° for 3 hours, cooled, subsequently poured into ice-water and extracted with methylene chloride. The methylene chloride extracts were dried over potassium carbonate and evaporated under reduced pressure, and the residue was chromatographed on 20 g of silica gel with a mixture of methylene chloride and isopropanol as the eluting agent. In this manner there were obtained 1.543 g of t-butyl [(1S,2S)-2-(t-butyldimethylsiloxy)-1-(cyclohexymethyl)-3-[[3-(ethoxycarbonyl)propyl]amino]propyl]carbamate as an oil which was used in the next step without further purification.

1.24 g (2.41 mmol) of t-butyl [(1S,2S)-2-(t-butyldimethylsiloxy)-1-(cyclohexymethyl)-3-[[3-ethoxycarbonyl)propyl]amino]propyl]carbamate were dissolved in 15 ml of ethanol and treated with 5.0 ml of 1N sodium hydroxide solution. The reaction mixture was thereafter stirred at room temperature for 2 hours, subsequently poured into water, acidified to pH 4.5 with acetic acid and extracted with methylene chloride. The methylene chloride extracts were dried over magnesium sulfate and evaporated under reduced pressure. Chromatography of the residue on 15 g of silica gel using a mixture of methylene chloride and methanol as the eluting agent yielded 687 mg of 4-[[(2S,3S)-3-(1-t-butoxyformamido)-2-(t-butoxydimethylsiloxy)-3-(cyclohexylmethyl)-propyl]amino]butyric acid in the form of a viscous oil which was used directly in the next step.

0.6 g (1.23 mmol) of 4-[[(2S,3S)-3-(1-t-butoxyformamido)-2-(t-butoxydimethylsiloxy)-3-(cyclohexylmethyl)propyl]amino]butyric acid was dissolved in 2 ml of methylene chloride and added dropwise at −20° to a solution of 285 mg of EDC and 200 mg of HOBT in 13 ml of methylene chloride. The reaction mixture was subsequently warmed to room temperature within 15 minutes, stirred at this temperature for 17 hours and subsequently poured into water and extracted with methylene chloride. The methylene chloride extracts were dried over magnesium sulfate, evaporated under reduced pressure and the residue was chromatographed on 10 g of silica gel using a mixture of methylene chloride and isopropanol as the eluting agent, whereby there were obtained 480 mg of t-butyl [(1S,2S)-2-(t-butyldimethylsiloxy)-1-(cyclohexylmethyl)-3-(2-oxo-1-pyrrolidinyl)propyl]carbamate as an oil which was used directly in the next step.

0.62 g (1.28 mmol) of t-butyl [(1S,2S)-2-(t-butyldimethylsiloxy)-1-(cyclohexylmethyl)-3-(2-oxo-1-pyrrolidinyl)propyl]carbamate was dissolved in 9 ml of acetonitrile in a polypropylene reaction vessel and treated at room temperature with 1.2 ml of 40% aqueous hydrofluoric acid. The reaction mixture was subsequently stirred at room temperature for 3 hours, thereafter poured into 2N sodium bicarbonate solution and extracted with methylene chloride. The methylene chloride extracts were dried over magnesium sulfate and evaporated under reduced pressure, whereby there were obtained 434 mg of t-butyl [(1S,2S)-1-(cyclohexylmethyl)-2-hydroxy-3-(2-oxo-1-pyrrolidinyl)propyl]carbamate as an oil which was used directly in the next step.

0.41 g (1.16 mmol) of t-butyl [(1S,2S)-1-(cyclohexylmethyl)-2-hydroxy-3-(2-oxo-1-pyrrolidinyl)propyl]carbamate was dissolved in 5 ml of methylene chloride, treated at 0° with 1.5 ml of 90% trifluoroacetic acid and subsequently stirred at room temperature for 5 hours. Thereafter, the reaction mixture was slowly added dropwise to 2N sodium carbonate solution, subsequently treated with 3N sodium hydroxide solution and finally extracted with methylene chloride. The methylene chloride extracts were dried over potassium carbonate and evaporated under reduced pressure, whereby there were obtained 249 mg of 1-[(2S,3S)-3-amino4-cyclohexyl-2-hydroxybutyl]-2-pyrrolidinone as an oil, MS: 255 (M+H)+.

220 mg (0.865 mmol) of 1-[(2S,3S)-3-amino-4-cyclohexyl-2-hydroxybutyl]-2-pyrrolidinone and 300 mg (0.618 mmol) of 1-(t-butoxycarbonyl)-N-[(R)-α-(3,3-dimethyl-2-oxobutyl)hydrocinnamoyl]-L-histidine were dissolved in 5 ml of methylene chloride, cooled to −20° and treated with 0.16 ml of N,N-diisopropylethylamine and 0.12 ml of diethyl cyanophosphonate. Thereupon, the reaction mixture was stirred at room temperature for 19 hours and subsequently poured into a mixture of ice and dilute sodium bicarbonate solution and extracted with methylene chloride. The methylene chloride extracts were dried over magnesium sulfate and evaporated, and the residue was chromatographed on 5 g of silica gel with a mixture of methylene chloride and isopropanol as the eluting agent, whereby there were obtained 430 g (96%) of (S)-N-[(1S,2S)-1-(cyclohexylmethyl)-2-hydroxy-3-(2-oxo-1-pyrrolidinyl)propyl]-α-[(R)-α-(3,3-dimethyl-2-oxobutyl)hydrocinnamamido]-3-t-butoxycarbonylimidazole-4propionamide as a yellow foam which was used directly in the next step.

EXAMPLE 5

In an analogous manner to that described in Example 4, (S)-N-[(1S,2S)-1-(cyclohexylmethyl)-2-hydroxy-3-(2-oxo-1-piperidinyl)propyl]-α-[(R)-α-(3,3-dimethyl-2-oxobutyl)hy drocinnamamido]-3-t butoxycarbonylimidazole-4-propionamide was treated with potassium carbonate in methanol, whereby there was obtained (S)-N-[(1S,2S)-1-(cyclohexylmethyl)-2-hydroxy-3-(2-oxopiperidino)propyl]-α-[(R)-α-(3,3-dimethyl-2-oxobutyl)hydrocinnamamido]imidazole-4propionamide as an amorphous solid, MS: 636 (M+H)+.

The (S)-N-[(1S,2S)-1-(cyclohexylmethyl)-2-hydroxy-3-(2-oxo-1-piperidinyl)propyl]-α-[(R)-α-(3,3-dimethyl-2-oxobutyl)hydrocinnamamido]-3-t-butoxycarbonylimidazole-4-propionamide used as the starting material was prepared in an analogous manner to that described in Example 4 from t-butyl [(S)-3-amino-(S)-2-(t-butyldimethylsiloxy)-1-(cyclohexylmethyl)propyl]-carbamate, whereby, however, ethyl 5-bromovalerate was used in place of ethyl 4-bromobutyrate.

EXAMPLE 6

The following compounds were prepared in an analogous manner to that described in Example 4:
From (S)-N-[(1S,2S)-1-(cyclohexylmethyl)-2-hydroxy-3
[methyl-[3-(phenylsulfonyl)propyl]amino]propyl]-α-[(R)-α-(3,3-dimethyl-2-oxobutyl)hydrocinnamamido]-3-t-butoxycarbonylimidazole-4-propionamide the (S)-N-[(1S,2S)-1-(cyclohexylmethyl)-2-hydroxy-3-[me-thyl[3-(phenylsulfonyl)propyl]amino]propyl]-α-[(R)-α-(3,3-dimethyl-2-oxobutyl)hydrocinnamamido]imidazole-4-propionamide as an amorphous solid, MS 750 (M+H))+;
from (S)-N-[(1S,2S)-1-(cyclohexylmethyl)-2-hydroxy-3-[methyl[6-(2-oxo-1-benzimidazolidinyl)hexyl]amino]propyl]-α-[(R)-α-(3,3-dimethyl-2-oxobutyl)hydrocinnamamido] -3-t-butoxycarbonylimidazole-4-propionamide the (S)-N-[(1S,2S)-1-(cyclohexylmethyl)-2-hydroxy-3
[methyl[6-(2-oxo-1-benzimidazolidinyl)hexyl]amino]]propyl]-α-[(R)-α-(3,3-dimethyl-2-oxobutyl)hydrocinnamamido]imidazole-4-propionamide as an amorphous solid, MS: 784 (M+H)+.
and
from (S)-N-[(1S,2S)-1-(cyclohexylmethyl)-3-[[4-(2-ethoxyethoxy)phenethyl]methylamino]propyl]-α-[(R)-α-(3,3-dimethyl-2-oxobutyl)hydrocinnamamido]-3-t-butoxycarbonylimidazole-4-propionamide the (S:R=2:1)-N-[(1S,2S)-1-(cyclohexylmethyl)-3-[[4-(2-ethoxyethoxy)phenethyl]methylamino]propyl]-α-[(R)-α-(3,3-dimethyl-2-oxobutyl)hydrocinnamamido]imidazole-4-propionamide dihydrochloride as an amorphous solid, MS: 760 (M+H)+.

The propionamides used as the starting materials were prepared as follows:

(S)-N-[(1S,2S)-1-(Cyclohexymethyl)-2-hydroxy-3[methyl-[3-(phenylsulphonyl)propyl]amino]propyl]-α-[(R)-α-(3,3-dimethyl-2-oxobutyl)hydrocinnamamido]-3-t-butoxycarbonylimidazole-4-propionamide This compound was prepared in analogy to Examples 1 and 2 by reacting t-butyl [(1S,2R:S=9:1)-1-(cyclohexylmethyl)-2,3-epoxypropyl]carbamate with N-methyl-3-(phenylsulfonyl)propylamine, cleaving off the Boc protecting group with trifluoroacetic acid (90%) in methylene chloride and reacting the (2S,3S)-3-amino-4-cyclohexyl-1[methyl-[3-(phenylsulfonyl)propyl]amino]-2-butanol obtained with 1-(t-butoxycarbonyl)-N-[(R)-α-(3,3-dimethyl-2-oxobutyl)hydrocinnamoyl]-L-histidine, (S)-N-[(1S,2,S)-1-(Cyclohexylmethyl)-2-hydroxy-3-[methyl[6-(2-oxo-1-benzimidazolidinyl)hexyl]amino]propyl]-α-[(R)-α-(3,3-dimethyl-2-oxobutyl)hydrocinnamamido]-3-t-butoxycarbonylimidazole-4-propionamide This compound was prepared, likewise in analogy to Examples 1 and 2, by reacting t-butyl [(1S,2R:S=9:1)-1-(cyclohexylmethyl)-2,3-epoxypropyl]carbamate with 1-[6-(methylamino)hexyl]-2-benzimidazolinone, cleaving off the Boc protecting group with 90% trifluoroacetic acid in methylene chloride and reacting the 1-[6-[[(2S,3S)-3-amino-2-hydroxy-4-cyclohexylbutyl]methylamino]hexyl]-2benzimidazolinone obtained with 1-(t-butoxycarbonyl)-N-(R)-α-(3,3-dimethyl-2-oxobutyl)hydrocinnamoyl]-L-histidine.

(S)-N-[(1S,2S)-1-(Cyclohexylmethyl)-3-[[4-(2-ethoxyethoxy)phenethyl]methylamino]propyl]-α-[(R)-α-(3,3-dimethyl-2-oxobutyl)hydrocinnamamido]-3-t-butoxycarbonylimidazole-4-propionamide This compound was also prepared in analogy to Examples 1 and 2 by reacting t-butyl [(1S,2R:S=9:1)-1-(cyclohexylmethyl)-2,3-epoxypropyl]carbamate with 4-(2-ethoxyethoxy)-N-methylphenethylamine, cleaving off the Boc protecting group with 1N hydrochloric acid in dioxan and reacting the (2S,3S)-3-amino-4-cyclohexyl-1-[[4-(2-ethoxyethoxy)phenethyl]methylamino]-2-butanol obtained with 1-(t-butoxycarbonyl)-N-[(R)-α-(3,3-dimethyl-2-oxobutyl)hydrocinnamoyl]-L-histidine.

The amines used as the starting materials were prepared as follows:

N-Methyl-3-(phenylsulphonyl)propylamine 25.5 g (71.9 mmol) of 3-(phenylsulfonyl)-1-propanol-4-methylbenzenesulfonate [see H. O. Fong et al., Can. J. Chem., 57, 1206 (1979)]were dissolved in 45 ml of methylamine and stirred for 24 hours at 80° and 1000 kpa. Thereafter, the methylamine was evaporated under reduced pressure, the residue was poured into ice-water and extracted with methylene chloride. The methylene chloride extracts were dried over potassium carbonate and evaporated under reduced pressure, whereby there were obtained 14.1 g of N-methyl-3-(phenylsulfonyl)-propylamine as an oil, MS: 214 (M+H)+.

4-(2-Ethoxyethoxy)-N-methylphenethylamine 90.12 g (1 mol) of 2-ethoxyethanol in 1.3 l of pyridine were treated at 0°-5° within 15 minutes with 114.5 g (1 mol) of methanesulfonyl chloride. The reaction mixture was stirred at the same temperature for 2 hours and then concentrated in a high vacuum. The residue was taken up in 1 l of ethyl acetate and the organic solution was washed with 2N hydrochloric acid and water, dried over sodium sulfate and evaporated. The thus-obtained 2-ethoxyethyl methanesulfonate was used in the next step without further purification.

3.06 g of a 55% sodium hydride dispersion in oil were washed with hexane and covered with 85 ml of dimethylformamide. 17.0 g (71.6 mmol) of t-butyl [4-hydroxyphenethyl]carbamate [see F. Rocchiccioli et al., Tetrahedron, 34, 2917 (1978)] were then added while cooling with ice and the reaction mixture was stirred at room temperature for 15 minutes. After cooling to 0° a solution of 12.04 g (71.6 mmol) of 2-ethoxyethyl methanesulfonate in 85 ml of dimethylformamide was added dropwise within 10 minutes and the reaction mixture was subsequently stirred at room temperature for 24 hours. Thereafter, the reaction mixture was poured into ice-water and extracted with methylene chloride. The methylene chloride extracts were dried over magnesium sulfate and evaporated under reduced pressure. The residue obtained was chromatographed on 240 g of silica gel with a mixture of hexane and ethyl acetate as the eluting agent and subsequently recrystallized from ether/hexane, whereby there were obtained 19.1 g of t-butyl [4-(2-ethoxyethoxy)phenethyl]carbamate, melting point 56°–57°.

3.2 g of a 55% sodium hydride dispersion in oil were washed with hexane and covered with 190 ml of dimethylformamide. Thereafter, 19.0 g (61.6 mmol) of t-butyl [4-(2-ethoxyethoxy)phenethyl]carbamate in solid form were added while cooling with ice and stirring, the reaction mixture was stirred at room temperature for 15 minutes and subsequently treated dropwise with 5.7 ml of methyl iodide in 10 ml of dimethylformamide within 5 minutes. After completion of the addition the reaction mixture was stirred at room temperature for 18 hours and subsequently poured into ice-water and extracted with methylene chloride. The methylene chloride extracts were dried over magnesium sulfate and evaporated under reduced pressure, and the residue was chromatographed on 240 g of silica gel with a mixture of hexane and ethyl acetate as the eluting agent, whereby 19.5 g of t-butyl [4-(2-ethoxyethoxy) phenethyl]-methylcarbamate were obtained as an oil which was used directly in the next step.

17.86 g (55.4 mmol) of t-butyl [4-(2-ethoxyethoxy)-phenethyl]methylcarbamate were dissolved in 350 ml of dioxan, treated with 66.4 ml of 1N hydrochloric acid solution and heated to reflux for 2 hours. Thereafter, the reaction mixture was concentrated, made alkaline with ammonia and extracted with a 4:1 mixture of methylene chloride and isopropanol. The organic extracts were dried over potassium carbonate and concentrated under reduced pressure, whereby there were obtained 12.1 g of 4-(2-ethoxyethoxy)-N-methylphenethylamine as an oil, MS: 180 (M-$C_2H_5N$)+.

EXAMPLE 7

A mixture of 170 mg (0.74 mmol) of ($\alpha$S,$\beta$S)-$\beta$-amino-$\alpha$-[(isopropylamino)methyl]cyclohexylpropanol, 796 mg (1.64 mmol) of 1-(t-butoxycarbonyl)-N-[(R)-$\alpha$-(3,3-dimethyl-2-oxobutyl)hydrocinnamoyl]-L-histidine, 0.46 ml (3.28 mmol) of triethylamine, 417 mg of BOPC and 20 ml of methylene chloride was stirred at room temperature for 2 days under argon. Thereafter, the reaction mixture was evaporated to dryness, the residue was dissolved in 20 ml of methanol, treated with 20 mg of potassium carbonate and stirred at room temperature for 2 hours. Then, the reaction mixture was evaporated to dryness and the residue was chromatographed on 50 g of silica gel with a 14:1:0.1 mixture of methylene chloride, methanol and ammonia as the eluting agent, whereby there were obtained 80 mg of (S)-N-[(1 S,2S)-1-(cyclohexylmethyl)-3-[(S)-$\alpha$-[(R)-$\alpha$-(3,3-dimethyl-2-oxobutyl)hydrocinnamamido]-N-isopropylimidazol-4-propionamido]-2-hydroxypropyl]-$\alpha$-[(R)-$\alpha$-(3,3-dimethyl-2-oxobutyl)hydrocinnamamido]imidazole-4-propionamide as a powdery solid, MS: 963 (M+H)+, and 270 mg of (RS)-N-[(1S,2S)-1-(cyclohexylmethyl)-2-hydroxy-3-(isopropylamino)propyl]-$\alpha$-[(R)-$\alpha$-(3,3-dimethyl-2-oxobutyl)hydrocinnamamido]imidazole-4-propionamide as a foam, MS: 596 (M+H)+.

The ($\alpha$S,$\beta$S)-$\beta$-amino-$\alpha$-[(isopropylamino)methyl]-cyclohexylpropanol used as the starting material was prepared as follows:

A mixture of 1.0 g (3.7 mmol) of t-butyl [(1S,2R:S=9:1)-1-(cyclohexylmethyl)-2,3-epoxypropyl]carbamate, 10 ml of methanol and 1.0 ml of isopropylamine was stirred at room temperature for 2 days. Subsequently, the reaction mixture was evaporated to dryness, the residue was treated with 20 ml of 3.6N hydrochloric acid in dioxan and the reaction mixture was left to stand at room temperature for 4 hours. Then, the solvent was evaporated and the residue was chromatographed on 50 g of silica gel with a 50:10:1 mixture of methylene chloride, methanol and ammonia as the eluting agent, whereby there were obtained 570 mg of ($\alpha$S,$\beta$S)-$\beta$-amino-$\alpha$-[(isopropylamino)methyl]cyclohexylpropanol as an oil, MS: 229 (M+H)+.

In an analogous manner to that described above, by reacting t-butyl [(1S,2R:S=9:1)-1-(cyclohexylmethyl)-2,3-epoxypropyl]carbamate with methylamine there was obtained [$\alpha$S,$\beta$S]-$\beta$-amino-$\alpha$-[(methylamino)methyl]cyclohexylpropanol as an oil, MS: 201 (M+H)+.

EXAMPLE 8

100 mg (0.168 mmol) of (RS)-N-[(1S,2S)-1-(cyclohexylmethyl)-2-hydroxy-3-(isopropylamino)propyl]-$\alpha$-[(R)-$\alpha$-(3,3-dimethyl-2-oxobutyl)hydrocinnamamido]imidazole-4-propionamide in 10 ml of methanol and 1 ml of triethylamine were treated with 100 mg of (Boc)$_2$O and left to stand at room temperature overnight. Thereafter, the reaction mixture was evaporated under reduced pressure and the residue was chromatographed on 30 g of silica gel with a 14:1:0.1 mixture of methylene chloride, methanol and ammonia as the eluting agent. Crystallization of the thus-obtained crude product (80 mg) from ether/hexane yielded 62 mg of t-butyl [(2S,3S)-4-cyclohexyl-3-[(R)-2-[(S)-$\alpha$-(3,3-dimethyl-2-oxobutyl)hydrocinnamamido]-3-(imidazol-4-yl)propionamido]-2-hydroxybutyl]isopropylcarbamate as a white solid, melting point 81°, MS: 696 (M+H)+.

EXAMPLE 9

A mixture of 100 mg (0.168 mmol) of (RS)-N-[(1S,2S)-1-(cyclohexylmethyl)-2-hydroxy-3-(isopropylamino)propyl]-$\alpha$-[(R)-$\alpha$-(3,3-dimethyl-2-oxobutyl)hydrocinnamamido]-imidazole-4-propionamide. 10 ml of tetrahydrofuran. 1 ml of triethylamine and 0.065 ml (0.5 mmol) of caproyl chloride was left to stand at room temperature overnight. Thereafter, the reaction mixture was evaporated under reduced pressure and extracted three times with 100 ml of ethyl acetate. The organic extracts were washed with 2N sodium bicarbonate solution and saturated sodium chloride solution, dried and evaporated. The residue was chromatographed on 30 g of silica gel with a 20:1:0.1 mixture of methylene chloride, methanol and ammonia as the eluting agent, whereby there were obtained 57 mg of (RS)-[(1S,2S)1-(cyclohexylmethyl)-2-hydroxy-3-N-isopropylhexanamido]-α-[(R)-α-(3,3-dimethyl-2-oxobutyl)hydrocinnamamido]-imidazole-4-propionamide as a foam, MS: 694 (M+H)+.

EXAMPLE 10

In an analogous manner to that described in Example 7, by reacting [αS,βS)-8-amino-α-[(methylamino)methyl]cyclohexylpropanol with 1-(t-butoxycarbonyl)-N-[(R)-α-(3,3-dimethyl-2-oxobutyl)hydrocinnamoyl]-L-histidine and cleaving off the Boc protecting group with potassium carbonate in methanol there were obtained (S)-N-[(1S,2S)-1-(cyclohexylmethyl)-2-hydroxy-3-[[(S)-1-[(S)-α-(3,3-dimethyl-2-oxobutyl)hydrocinnamamido]-2-imidazol-4-yl-ethyl]methylamino]-propyl]-α-[(R)-α-(3,3-dimethyl-2-oxobutyl)hydrocinnamamido]imidazole-4-propionamide in the form of a white solid, melting point 118°, MS: 935 (M+H)+, as the more polar component as well as (RS)-N-[(1S,2S)-1-(cyclohexylmethyl)-2-hydroxy-3-(methylamino)-propyl]-α-[(R)-α-(3,3-dimethyl-2-oxobutyl)hydrocinnamamido]imidazole-4-propionamide as the less polar component.

EXAMPLE 11

120 mg (0.2 mmol) of (RS)-N-[(1S,2S)-1-(cyclohexylmethyl)-2-hydroxy-3-(methylamino)propyl]-α-[(R)-α-(3,3-dimethyl-2-oxobutyl)hydrocinnamamido]imidazole-4propionamide were reacted with 1-(t-butoxycarbonyl)-N-(t-butoxycarbonyl)-L-histidine in an analogous manner to that described in Example 7. Then, the reaction mixture was evaporated and the residue was left to stand at room temperature in 20 ml of 3.6N hydrochloric acid in dioxan for 2 hours. Thereafter, the reaction mixture was evaporated and the residue was reacted with hydrocinnamoyl chloride in an analogous manner to that described in Example 9. Working-up of the reaction mixture, likewise in an analogous manner to that described in Example 9, yielded a crude product which was chromatographed on 30 g of silica gel with a 140:1:0.1 mixture of methylene chloride, methanol and ammonia as the eluting agent. Crystallization of the thus-obtained crude product (77 mg) from methylene chloride/hexane yielded (S)-N-[(1S,2S)-1-(cyclohexylmethyl)-2-hydroxy-3-[(S)-3-(imidazol-4-yl)-2-hydrocinnamamido-N-methylpropionamido]propyl]-α-[(R)-α-(3,3-dimethyl-2-oxobutyl)hydrocinnamamido]-imidazole-4-propionamide as a white solid, melting point 109°, MS: 837 (M+H)+.

EXAMPLE 12

In an analogous manner to that described in Example 7, by reacting [αS,βS)-β-amino-α-[(methylamino)methyl]cyclohexylpropanol with 1-(t-butoxycarbonyl)-N-(t butoxycarbonyl)-L-histidine and cleaving off the Boc protecting group there were obtained t-butyl [(S)-1-[[(2S,3S)-4-cyclohexyl-3-[(S)-2-(1-t-butoxyformamido)-2-imidazol-4-ylpropionamido]butyl]carbamoyl]-2-imidazol-4-ylethyl]carbamate as a white solid, MS: 675 (M+H)+, and t-butyl [(S)-1-[[(1S.2S)-1-(cyclohexylmethyl)-2-hydroxy 3-(methylamino)propyl]carbamoyl]-2-imidazol-4-ylethyl]carbamate as a foam, MS: 537 (M+H)+.

EXAMPLE 13

In an analogous manner to that described in Example 11, by reacting t-butyl [(S)-1-[[(1S,2S)-1-(cyclohexylmethyl)-2-hydroxy-3-(methylamino)propyl]carbamoyl]-2-imidazol-4-ylethyl]carbamate with Boc-Phe-OH there was obtained t-butyl [(S)-α-[[(2S,3S)-3-[(S)-2-[(S)-α-(1-t-butoxyformamido)hydrocinnamamido]-3-imidazol-4-ylpropionamido]-4-cyclohexyl-2-hydroxybutyl]methylcarbamoyl]phenethyl]carbamate as a white solid, MS: 832 (M+H)+.

EXAMPLE 14

In an analogous manner to that described in Example 11, by cleaving off the Boc protecting group from t-butyl [(S)-1-[[(2S,3S)-4-cyclohexyl-3-[(S)-2-(1-t-butoxyformamido)-2-imidazol-4-ylpropionamido]butyl]carbamoyl]-2-imidazol-4-ylethyl]carbamate and subsequently reacting with Boc-Phe-OH there was obtained t-butyl [(S)-α-[[(S)-1-[[(1S,2S)-3-[[(S)-1-[(S)-α-(1-t-butoxyformamido)hydrocinnamamido]-2-imidazol-4 ylethyl]methylcarbamoyl]-1-(cyclohexylmethyl)-2-hydroxypropyl]carbamoyl]-2-imidazol-4-ylethyl]carbamoyl]phenethyl]carbamate as a white solid, MS: 969 (M+H)+.

EXAMPLE 15

50 mg (0.08 mmol) of (S)-N-[(1S,2S)-3-amino-1-(cyclohexylmethyl)-2-hydroxypropyl]-α-[(R)-α-(3,3-dimethyl-2-oxobutyl)hydrocinnamamido]imidazole-4-propionamide hydrochloride and 1.5 g (10 mmol) of phthalic anhydride were suspended in 15 ml of acetonitrile and heated to reflux overnight. Thereafter, the reaction mixture was evaporated to dryness under reduced pressure and the residue was chromatographed on 10 g of silica gel with a mixture of methylene chloride, methanol and ammonia as the eluting agent, whereby there were obtained 31 mg of (S)-N[(1S,2S)-1-(cyclohexylmethyl)-2-hydroxy-3-phthalimidopropyl]-α-[(R)-α-(3,3-dimethyl-2-oxobutyl)hydrocinnamamido]imidazole-4-propionamide as a foam, MS: 684 (M+H)+.

EXAMPLE 16

In an analogous manner to that described in Example 4 by cleaving off the Boc protecting group from (S)-N-[(1S, 2RS)-1-(cyclohexylmethyl)-2-hydroxy-3-nitropropyl]-α-[(R)-α-(3,3-dimethyl-2-oxobutyl)hydrocinnamamido]-3-t-butoxycarbonylimidazole-4-propionamide with potassium carbonate in methanol and subsequently purifying by chromatography on 50 g of silica gel using a 200:10:1 mixture of methylene chloride, methanol and ammonia as the eluting agent there were obtained the two epimeric compounds (S)-N-[(1S,2S or R)-1-(cyclohexylmethyl)-2-hydroxy-3-nitropropyl]-α-[(R)-α-(3 3-dimethyl-2-oxobutyl)hydrocinnamamido]imidazole-4-propionamide and (S)-N[(1S,2R or S)-1-(cyclohexylmethyl)-2-hydroxy-3-nitropropyl]-α-[(R)-α-(3.3-dimethyl-2-oxobutyl)hydrocinnamamido]imidazole-4-propionamide, in both cases as a foam, MS (each): 584 (M+H)+.

The (S)-N-[(1S,2RS)-1-(cyclohexylmethyl)-2-hydroxy-3-nitropropyl]-α-[(R)-α-(3,3-dimethyl-2-oxobutyl)hydrocinnamamido]-3-t-butoxycarbonylimidazole-4-propionamide used as the starting material was prepared as follows:

306.8 mg of a 65% sodium hydride dispersion in oil were added to 0.40 ml (7.5 mmol) of nitromethane in 5 ml of tetrahydrofuran and the reaction mixture was held at 50° for one hour. Thereafter, the reaction mixture was cooled to −78° and treated dropwise with a solution of 383 mg (1.5 mmol) of 2-t-butoxycarbonylamino-3(S)-cyclohexyl-propylaldehyde in 5 ml of tetrahydrofuran. Thereafter, the cooling bath was removed, the mixture was left to stand for a further 3 hours, then poured on to ice and extracted three times with 120 ml of ethyl acetate. The ethyl acetate extracts were washed with 60 ml of saturated sodium chloride solution, dried over magnesium sulfate and evaporated. Chromatography of the crude product obtained (390 mg) on 35 g of silica gel using a 95:5 mixture of toluene and ethyl acetate as the eluting agent yielded 170 mg of t-butyl [(1S,2RS)-1-(cyclohexylmethyl)-3-hydroxy-3-nitropropyl]carbamate as an oil, MS: 317 (M+H)+.

In an analogous manner to that described in Example 7, by cleaving off the Boc protecting group from t-butyl [(1S,2RS)-1-(cyclohexylmethyl)-2-hydroxy-3-nitropropyl]carbamate with hydrochloric acid in dioxan and reacting the intermediately-obtained [(1S,2RS)-2-amino-1-(cyclohexylmethyl)-4-nitrobutan-3-ol with 1-(t-butoxycarbonyl)-N-[(R)-α-(3  3-dimethyl-2-oxobutyl)hydrocinnamoyl]-L-histidine there was obtained (S)-N-[(1S,2RS)-1-(cyclohexylmethyl)-2-hydroxy-3-nitropropyl]-α-[(R)-α-(3,3-dimethyl-2-oxobutyl)hydrocinnamamido]-3-t-butoxycarbonylimidazole-4-propionamide which was used directly in the next step.

EXAMPLE A

A sterile-filtered aqueous solution of t-butyl [(S)-α-[[(S)-1-[[(1S,2S)-3-[[(S)-1-[(S)-α-(1-t-butoxyformamido)-hydrocinnamamido]-2-imidazol-4-ylethyl]methylcarbamoyl]-1-(cyclohexylmethyl)-2-hydroxypropyl]carbamoyl]2-imidazol-4-ylethyl]carbamoyl]phenethyl]carbamate is mixed while warming with a sterile gelatin solution, which contains phenol as a preserving agent, under aseptic conditions so that 1.0 ml of solution has the following composition:

| | |
|---|---|
| t-Butyl [(S)-α-[[(S)-1-[[(1S,2S)-3-[[(S)-1-[(S)-α-(1-t-butoxyformamido)-hydrocinnamamido]-2-imidazol-4-ylethyl]-methylcarbamoyl]-1-(cyclohexylmethyl)-2-hydroxypropyl]carbamoyl]-2-imidazol-4-ylethyl]carbamoyl]phenethyl]carbamate | 3.0 mg |
| Gelatine | 150.0 mg |
| Phenol | 4.7 mg |
| Dist. water ad | 1.0 ml |

The mixture is filled into 1.0 ml vials under aseptic conditions.

EXAMPLE B 5 mg of t-butyl [(S)-α-[[(S)-1-[[(1S,2S)-3-[[(S)-1-[(S)-α-(1-t-butoxyformamido)hydrocinnamamido]-2-imidazol-4-ylethyl]methylcarbamoyl]-1-(cyclohexylmethyl) 2-hydroxypropyl]carbamoyl]-2-imidazol-4-ylethyl]carbamoyl]phenethyl]carbamate are dissolved in 1 ml of an aqueous solution with 20 mg of mannitol. The solution is filtered sterile and filled under aseptic conditions into a 2 ml ampoule, cooled to a low temperature and lyophilized. Prior to administration the lyophilizate is dissolved in 1 ml of distilled water or 1 ml of physiological saline. The solution is used intramuscularly or intravenously. This formulation can also be filled into double chamber injection ampoules.

EXAMPLE C 500 mg of finely milled (5.0 μm) t-butyl [(S)-α-[[(S)-1-[[(1S,2S)-3-[[(S)-1-[(S)-α-(1-t-butoxyformamido)hydrocinnamamido]-2-imidazol-4-ylethyl]methylcarbamoyl]-1-(cyclohexylmethyl)-2-hydroxypropyl]carbamoyl]-2-imidazol-4-ylethyl]carbamoyl]phenethyl]carbamate are suspended in a mixture of 3.5 ml of Myglyol 812 and 0.08 g of benzyl alcohol. This suspension is filled into a container having a dosage valve. 5.0 g of Freon 12 are filled into the container through the valve under pressure. The Freon is dissolved in the Myglyol-benzyl alcohol mixture by shaking. This spray container contains about 100 individual dosages which can be applied individually.

EXAMPLE D

When the procedures described in Examples A-C are followed, corresponding galenical preparations can be prepared from the following, likewise preferred, compounds:

(S)-N-[(1S,2S)-1-(Cyclohexylmethyl)-2-hydroxy-3-(2-oxopiperidino)propyl]-α-[(R)-α-(3,3-dimethyl-2-oxobutyl)hydrocinnamamido]imidazole-4-propionamide;

(S)-N-[(1S,2S)-1-(cyclohexylmethyl)-3-[(S)-α-[(R)-α-(3.3-dimethyl-2-oxobutyl)hydrocinnamamido]-N-isopropylimidazol-4-propionamido]-2-hydroxypropyl]-α-[(R)-α-(3,3-dimethyl-2-oxobutyl)hydrocinnamamido]imidazole-4-propionamide;

(S)-N-[(1S,2S)-1-(cyclohexylmethyl)-2-hydroxy-3 [[(S)-1-[(S)-α-(3,3-dimethyl-2-oxobutyl)hydrocinnamamido]-2-imidazol-4-ylethyl]methylamino]-propyl]-α-[(R)-α-(3,3-dimethyl-2-oxobutyl)hydrocinnamamido]imidazole-4-propionamide;

(S)-N-[(1S.2S)-1-(cyclohexylmethyl)-2-hydroxy-3-[(S)3-(imidazol-4-yl)-2-hydrocinnamamido-N-methylpropionamido]propyl]-α-[(R)-α-(3.3-dimethyl-2-oxobutyl)hydrocinnamamido]imidazole-4-propionamide;

t-butyl [(S)-α-[[(2S.3S)-3-[(S)-2-[(S)-α-(1-t-butoxyformamido)hydrocinnamamido]-3-imidazol-4-ylpropionamido]-4-cyclohexyl-2-hydroxybutyl]methylcarbamoyl]phenethyl]carbamate and (S)-N-[(1S.2S)-1-(cyclohexylmethyl)-2-hydroxy-3-phthalimidopropyl]-α-[(R)-α-(3.3-dimethyl-2-oxobutyl)hydrocinnamamido]imidazole-4-propionamide.

We claim:

1. An amino acid derivative of the formula

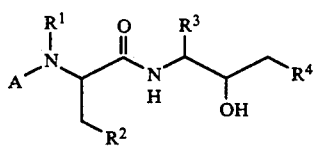

wherein R¹ is hydrogen or methyl; R² is ethyl, propyl, isopropyl, imidazol-2-yl, imidazol-4-yl, pyrazol-3-yl, thiazol-4-yl, thien-2-yl, ethoxycarbonyl, t-butylcarbonylmethyl, benzyloxycarbonylmethyl or t-butoxy; R³ is isobutyl, cyclohexylmethyl or benzyl; R⁴ is a group of the formula —N(R⁵)(R⁶); and A is one of the groups

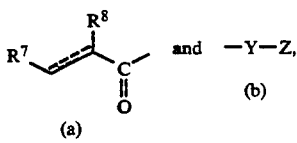

wherein $R^5$ is alkyl; $R^6$ is an acyl radical of an amino acid or a dipeptide, which amino acid or dipeptide is unsubstituted or substituted N-terminally by an acyl of a carboxylic acid; $R^7$ is phenyl, phenyl which is mono- or multiply-substituted with alkyl, alkoxy, alkoxyalkoxy, alkanoyl, alkanoyloxy, hydroxy, halogen or trifluoromethyl, or benzyl or naphthyl; and $R^8$ is hydrogen, alkoxycarbonylalkyl, alkylcarbonylalkyl, cycloalkylcarbonylalkyl, heterocycloalkylcarbonylalkyl, arylcarbonylalkyl, aminocarbonylalkyl, substituted aminocarbonylalkyl, aminoalkylcarbonylalkyl, substituted aminoalkylcarbonylalkyl, aminoalkylsulfonylalkyl, substituted aminoalkylsulfonylalkyl, alkoxycarbonylhydroxyalkyl, alkylcarbonylhydroxyalkyl, cycloalkylcarbonylhydroxyalkyl, heterocycloalkylcarbonylhydroxyalkyl, arylcarbonyl-hydroxyalkyl, aminocarbonyl-hydroxyalkyl, substituted aminocarbonylhydroxyalkyl, dialkoxyphosphoroxyalkyl, diphenyl-oxyphosphoroxyalkyl, arylalkyl, alkoxycarbonylamino, arylalkoxycarbonylamino, alkylthioalkythioalkyl, alkylsulfinylalkyl, alkylsulfonylalkyl, arylthioalkyl, arylsulfinylalkyl, arylsulfonylalkyl, arylalkylthioalkyl, arylalkylsulfinylalkyl or arylalkylsulfonylalkyl, where the substituted amino portion of the above $R^8$ moieties ia an amino group which is mono- or di-substituted by alkyl, arylalkyl, alkanoyl, alkoxycarbonyl or arylalkoxycarbonyl, or di-substituted by $C_3$–$C_6$-alkylene or $C_3$–$C_6$-alkylene which is interrupted by an oxygen, sulfur or nitrogen atom, the nitrogen atom being an unsubstituted or substituted with alkyl, phenylalkyl, alkanoyl or alkanoyloxy, with the proviso that $R^8$ is not alkoxycarbonylamino or arylalkoxycarbonylamino when $R^7$ is phenyl, benzyl or α-naphthyl; Y is a bivalent acyl radical or phenylglycine, cyclohexylglycine, phenylalanine, cyclohexylalanine, 4-fluorophenylalanine, 4-chlorophenylalanine, tyrosine, O-methyltyrosine, α-naphthylalanine or homophenylalanine, each of which is N- or α-methylated and is linked with Z at the N-terminal; and Z is hydrogen or an acyl of a carboxylic acid, in the form of optically pure diastereomers, mixtures of diastereomers, diastereomeric racemates or mixtures of diastereomeric racemates or a pharmaceutically usable salt of such compound.

2. A compound in accordance with claim 1, wherein $R^1$ is hydrogen.

3. A compound in accordance with claim 1, wherein $R^2$ is imidazol-2-yl, imidazol-4-yl or thiazol-4-yl.

4. A compound in accordance with claim 3 wherein $R^2$ is imidazol-4-yl.

5. A compound in accordance with claim 1, wherein $R^3$ is cyclohexylmethyl.

6. A compound in accordance with claim 1, wherein A is group (a).

7. A compound in accordance with claim 6, wherein $R^7$ is phenyl.

8. A compound in accordance with claim 6 wherein $R^7$ is phenyl being mono- or multiply-substituted with alkyl, alkoxy, alkoxyalkoxy, alkanoyl, alkanoyloxy, hydroxy, halogen or trifluoromethyl.

9. A compound in accordance with claim 6 wherein $R^8$ is alkylcarbonylalkyl, aminoalkylcarbonylalkyl, substituted aminoalkylcarbonylalkyl, aminoalkylsulfonylalkyl, substituted aminoalkylsulfonylalkyl or alkylsulfonylalkyl.

10. A compound in accordance with claim 9 wherein $R^8$ is alkylcarbonylalkyl or alkylsulfonylakyl.

11. A compound in accordance with claim 10 wherein $R^8$ is $C_1$–$C_4$-alkylcarbonylmethyl or $C_1$–$C_4$-alkylsulfonylmethyl.

12. A compound in accordance with claim 1 wherein $R^5$ is methyl; and $R^6$ is the acyl radical of histidine or phenylalanine which is substituted N-terminally by the acyl of a carboxylic acid, or an acyl radical of the dipeptide from histidine and phenylalanine which is substituted N-terminally by the acyl of a carboxylic acid.

13. A compound in accordance with claim 1, wherein $R^1$ is hydrogen; $R^2$ is imidazol-4-yl; $R^3$ is cyclohexylmethyl; $R^4$ is the group —N($R^5$)($R^6$); $R^5$ is methyl; $R^6$ is the acyl radical of histidine or phenylalanine which is substituted N-terminally by the acyl of a carboxylic acid, or the acyl radical of the dipeptide from histidine and phenylalanine which is substituted N-terminally by the acyl of a carboxylic acid; $R^7$ is phenyl; and $R^8$ is $C_1$–$C_4$-alkylcarbonylmethyl or $C_1$–$C_4$-alkylsulfonylmethyl.

14. A compound in accordance with claim 1 from a group comprising:
(S)-N-[(1S,2S)-1-(cyclohexylmethyl)-2-hydroxy-3-(2-oxopiperidino)propyl]-α-[(R)-α-(3,3-dimethyl-2-oxobutyl)hydrocinnamamido]imidazole-4-propionamide,
(S)-N-[(1S,2S)-1-(cyclohexylmethyl)-3-[(S)-α-[(R)-α-(3,3-dimethyl-2-oxobutyl)hydrocinnamamido]-N-isopropylimidazol-4-propionamido]-2-hydroxypropyl]-α-[(R)-α-(3,3-dimethyl-2-oxobutyl)hydrocinnamamido]imidazole-4-propionamide,
(S)-N-[(1S,2S)-1-(cyclohexylmethyl)-2-hydroxy-3-[[(S)-1-[(S)-α-(3,3-dimethyl-2-oxobutyl)hydrocinnamamido]-2-imidazol-4-ylethyl]methylamino]propyl]-α-[(R)-α-(3,3-dimethyl-2-oxobutyl)hydrocinnamamido]imidazole-4-propionamide,
(S)-N-[(1S,2S)-1-(cyclohexylmethyl)-2--hydroxy-3-[(S)--3-(imidazol-4-yl)-2-hydrocinnamamido-N---methylpropionamido]propyl]-α-[(R)-α-(3,3-dimethyl-2-oxobutyl)hydrocinnamamido]imidazole-4-propionamide,
t-butyl [(S)-α-[[(S)-1-[[(1S,2S)-3-[[(S)-1-[(S)-α-(1--t-butoxyformamido)hydrocinnamamido]-2-imidazol-4-ylethyl]methylcarbamoyl]-1-(cyclohexylmethyl)-2-hydroxypropyl]carbamoyl]-2-imidazol-4-ylethyl]carbamoyl]phenethyl]carbamate,
t-butyl [(S)-α-[[(2S,3S)-3-[(S)-2-[(S)-α-(1-t-butoxyformamido)hydrocinnamamido]-3-imidazol-4-yl-propionamido]-4-cyclohexyl-2-hydroxybutyl]methylcarbamoyl]phenethyl]carbamate and
(S)-N-[(1S,2S)-1-(cyclohexylmethyl)-2-hydroxy-3-phthalimidopropyl]-α-[(R)-α-(3,3-dimethyl-2-oxobutyl)hydrocinnamamido]imidazole-4-propionamide.

15. A composition for treating or preventing high blood pressure or cardiac insufficiency comprising an effective amount of a compound of the formula

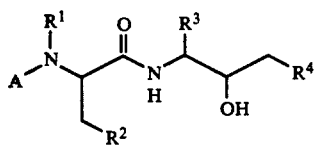

wherein $R^1$ is hydrogen or methyl; $R^2$ is ethyl, propyl, isopropyl, imidazol-2-yl, imidazol-4-yl, pyrazol-3-yl, thiazol-4-yl, thien-2-yl, ethoxycarbonyl, t-butylcarbonylmethyl, benzyloxycarbonylmethyl or t-butoxy; $R^3$ is isobutyl, cyclohexylmethyl or benzyl; $R^4$ is a group of the formula $-N(R^5)(R^6)$; and A is one of the groups

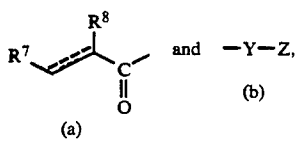

wherein $R^5$ is alkyl, $R^6$ is an acyl radical or an amino acid or a dipeptide, which amino acid or dipeptide is unsubstituted or substituted N-terminally by an acyl of a carboxylic acid; $R^7$ is phenyl, phenyl which is mono- or multiply-substituted with alkyl, alkoxy, alkoxyalkoxy, alkanoyl, alkanoyloxy, hydroxy, halogen or trifluoromethyl, or benzyl or naphthyl; and $R^8$ is hydrogen, alkoxycarbonylalkyl, alkylcarbonylalkyl, cycloalkylcarbonylalkyl, heterocycloalkylcarbonylalkyl, arylcarbonylalkyl, aminocarbonylalkyl, substituted aminocarbonylalkyl, aminoalkylcarbonylalkyl, substituted aminoalkylcarbonylalkyl, aminoalkylsulfonylalkyl, substituted aminoalkylsulfonylalkyl, alkoxycarbonylhydroxyalkyl, alkylcarbonylhydroxyalkyl, cycloalkylcarbonylhydroxyalkyl, heterocycloalkylcarbonylhydroxyalkyl, arylcarbonyl-hydroxyalkyl, aminocarbonyl-hydroxyalkyl, substituted aminocarbonylhydroxyalkyl, dialkoxyphosphoroxyalkyl, diphenyl-oxyphosphoroxyalkyl, arylalkyl, alkoxycarbonylamino, arylalkoxycarbonylamino, alkylthioalkyl, alkylsulfinylalkyl, alkylsulfonylalkyl, arylthioalkyl, arylsulfinylalkyl, arylsulfonylalkyl, arylalkylthioalkyl, arylalkylsulfinylalkyl or arylalkylsulfonylalkyl, where the substituted amino portion of the above $R^8$ moieties is an amino group which is mono- or di-substituted by alkyl, arylalkyl, alkanoyl, alkoxycarbonyl or arylalkoxycarbonyl, or di-substituted by $C_3-C_6$-alkylene or $C_3-C_6$-alkylene which is interrupted by an oxygen, sulfur or nitrogen atom, the nitrogen atom being an unsubstituted or substituted with alkyl, phenylalkyl, alkanoyl or alkanoyloxy, with the proviso that $R^8$ is not alkoxycarbonylamino or arylalkoxycarbonylamino when $R^7$ is phenyl, benzyl or α-naphthyl; Y is a bivalent acyl radical or phenylglycine, cyclohexylglycine, phenylalanine, cyclohexylalanine, 4-fluorophenylalanine, 4-chlorophenylalanine, tyrosine, O-methyltyrosine, α-naphthylalanine or homophenylalanine, each of which is N- or α-methylated and is linked with Z at the T-terminal; and Z is hydrogen or an acyl of a carboxylic acid, in the form of optically pure diastereomers, mixtures of diastereomers, diastereomeric racemates or mixtures of diastereomeric racemates or a pharmaceutically usable salt of such compound.

16. A method for treating or preventing high blood pressure or cardiac insufficiency in a patient in need of such treatment comprising administering an effective amount of a compound of the formula

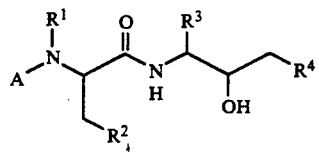

wherein $R^1$ is hydrogen or methyl; $R^2$ is ethyl, propyl, isopropyl, imidazol-2-yl, imidazol-4-yl, pyrazol-3-yl, thiazol-4-yl, thien-2-yl, ethoxycarbonyl, t-butylcarbonylmethyl, benzyloxycarbonylmethyl or t-butoxy; $R^3$ is isobutyl, cyclohexylmethyl or benzyl; $R^4$ is a group of the formula $-N(R^5)(R^6)$; and A is one of the groups

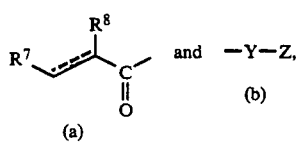

wherein $R^5$ is alkyl; $R^6$ is an acyl radical of an amino acid or a dipeptide, which amino acid or dipeptide may be unsubstituted or substituted N-terminally by an acyl of a carboxylic acid; $R^7$ is phenyl, phenyl which is mono- or multiply-substituted with alkyl, alkoxy, alkoxyalkoxy, alkanoyl, alkanoyloxy, hydroxy, halogen or trifluoromethyl, or benzyl or naphthyl; and $R^8$ is hydrogen, alkoxycarbonylalkyl, alkylcarbonylalkyl, cycloalkylcarbonylalkyl, heterocycloalkylcarbonylalkyl, arylcarbonylalkyl, aminocarbonylalkyl, substituted aminocarbonylalkyl, aminoalkylcarbonylalkyl, substituted aminoalkylcarbonylalkyl, aminoalkylsulfonylalkyl, substituted aminoalkylsulfonylalkyl, alkoxycarbonylhydroxyalkyl, alkylcarbonylhydroxyalkyl, cycloalkylcarbonylhydroxyalkyl, heterocycloalkylcarbonylhydroxyalkyl, arylcarbonyl-hydroxyalkyl, aminocarbonyl-hydroxyalkyl, substituted aminocarbonylhydroxyalkyl, dialkoxyphosphoroxyalkyl, diphenyl-oxyphosphoroxyalkyl, arylalkyl, alkoxycarbonylamino, arylalkoxycarbonylamino, alkylthioalkyl, alkylsulfinylalkyl, alkylsulfonylalkyl, arylthioalkyl, arylsulfinylalkyl, arylsulfonylalkyl, arylalkylthioalkyl, arylalkylsulfinylalkyl or arylalkylsulfonylalkyl, where the substituted amino portion of the above $R^8$ moieties is an amino group which is mono- or di-substituted by alkyl, arylalkyl, alkanoyl, alkoxycarbonyl or arylalkoxycarbonyl, or disubstituted by $C_3-C_6$-alkylene which can be interrupted by an oxygen, sulfur or nitrogen atom, the nitrogen atom being unsubstituted or substituted with alkyl, phenylalkyl, alkanoyl or alkanoyloxy, with the proviso that $R^8$ is not alkoxycarbonylamino or arylalkoxycarbonylamino when $R^7$ is phenyl, benzyl or α-naphthyl; Y is a bivalent acyl radical of phenylglycine, cyclohexylglycine, phenylalanine, cyclohexylalanine, 4-fluorophenylalanine, 4-chlorophenylalanine, tyrosine, O-methyltyrosine, α-naphthylalanine or homophenylalanine, each of which may be N- or α-methylated and is lined with Z at the N-terminal; and Z is hydrogen or an acyl of a carboxylic acid, in the form of optically pure diastereomers, mixtures of diastereomers, diastereomeric racemates or mixtures of diastereomeric racemates or a pharmaceutically usable salt of such compound.

* * * * *

UNITED STATES PATENT AND TRADEMARK OFFICE
CERTIFICATE OF CORRECTION

PATENT NO. : 5,278,148
DATED     : January 11, 1994
INVENTOR(S) : Quirico Branca, Hans P. Marki, Werner Neidhart, Henri Ramuz and Wolfgang Wostl It is certified that error appears in the above-identified patent and that said Letters Patent is hereby corrected as shown below:

In claim 1, column 29, line 27, delete "alkylthioalkylthioalkyl" and insert therefor -- alkylthioalkyl --;

In claim 1, column 29, line 31, delete "ia" and insert therefor -- is --;

In claim 10, column 30, line 6, delete "alkylsulfonylakyl" and insert therefor -- alkylsulfonylalkyl --;

In claim 14, column 30, line 46, delete "-2--" and insert therefor -- -2- --

In claim 14, column 30, line 47, delete "-N--" and insert therefor -- -N- --;

In claim 15, column 31, line 57, delete "or" and insert therefor -- of --.

Signed and Sealed this

Twelfth Day of July, 1994

Attest:

BRUCE LEHMAN

Attesting Officer    Commissioner of Patents and Trademarks